United States Patent
Cappadona et al.

(10) Patent No.: US 12,023,105 B2
(45) Date of Patent: Jul. 2, 2024

(54) SYSTEM, DEVICES AND METHOD FOR SURGICAL NAVIGATION INCLUDING ACTIVE TRACKING AND DRIFT ELIMINATION

(71) Applicant: Neurosimplicity, LLC, Colts Neck, NJ (US)

(72) Inventors: Anthony Cappadona, Clark, NJ (US); Jared Rosenblum, Colts Neck, NJ (US); Stephen Stasiulewicz, Linden, NJ (US); Matthew Nazari, Great Falls, VA (US)

(73) Assignee: Neurosimplicity, LLC, Colts Neck, NJ (US)

( * ) Notice: Subject to any disclaimer, the term of this patent is extended or adjusted under 35 U.S.C. 154(b) by 1399 days.

(21) Appl. No.: 16/326,968

(22) PCT Filed: Aug. 22, 2017

(86) PCT No.: PCT/US2017/048003
§ 371 (c)(1),
(2) Date: Feb. 21, 2019

(87) PCT Pub. No.: WO2018/039223
PCT Pub. Date: Mar. 1, 2018

(65) Prior Publication Data
US 2019/0183589 A1  Jun. 20, 2019

Related U.S. Application Data

(60) Provisional application No. 62/455,838, filed on Feb. 7, 2017, provisional application No. 62/455,186, filed
(Continued)

(51) Int. Cl.
*A61B 8/00* (2006.01)
*A61B 34/10* (2016.01)
(Continued)

(52) U.S. Cl.
CPC .............. *A61B 34/20* (2016.02); *A61B 34/10* (2016.02); *A61B 90/10* (2016.02); *A61B 90/14* (2016.02);
(Continued)

(58) Field of Classification Search
CPC ... A61B 34/20; A61B 34/10; A61B 2034/105; A61B 2034/108; A61B 2034/2048;
(Continued)

(56) References Cited

U.S. PATENT DOCUMENTS

2005/0194973 A1  9/2005  Kwon et al.
2006/0229641 A1  10/2006  Gupta et al.
(Continued)

FOREIGN PATENT DOCUMENTS

EP            1510182 A2    1/2010

OTHER PUBLICATIONS

Written opinion for PCT/US2017/048003 dated Dec. 7, 2017.
(Continued)

*Primary Examiner* — Joel F Brutus
(74) *Attorney, Agent, or Firm* — Agris & von Natzmer LLP; Joyce von Natzmer

(57) ABSTRACT

A neuro-navigation accessory system includes components programmed to work with existing neural navigational software. The components include trackers or motion sensors, modified surgical instruments with motion sensors incorporated into the instruments, CT/MRI opaque fiducial(s), surgical head clamps(s), ready-to-use, surgery specific kits, magnetic-field calibration apparatus for magnetic navigation, and internal reference arrays.

25 Claims, 13 Drawing Sheets

Related U.S. Application Data on Feb. 6, 2017, provisional application No. 62/378,415, filed on Aug. 23, 2016.

(51) Int. Cl.
*A61B 34/20* (2016.01)
*A61B 90/00* (2016.01)
*A61B 90/10* (2016.01)
*A61B 90/14* (2016.01)

(52) U.S. Cl.
CPC ........ *A61B 90/36* (2016.02); *A61B 2034/105* (2016.02); *A61B 2034/108* (2016.02); *A61B 2034/2048* (2016.02); *A61B 2034/2051* (2016.02); *A61B 2090/3983* (2016.02); *A61B 2090/3995* (2016.02)

(58) Field of Classification Search
CPC . A61B 2034/2051; A61B 90/10; A61B 90/14; A61B 90/36; A61B 2090/3983; A61B 2090/3995
See application file for complete search history.

(56) References Cited

U.S. PATENT DOCUMENTS

| | | |
|---|---|---|
| 2007/0197895 A1 | 8/2007 | Nycz et al. |
| 2007/0225550 A1 | 9/2007 | Gattani et al. |
| 2011/0320153 A1 | 12/2011 | Lightcap et al. |
| 2014/0135616 A1 | 5/2014 | Stein et al. |
| 2014/0135773 A1 | 5/2014 | Stein et al. |
| 2014/0276855 A1 | 9/2014 | de la Barrera et al. |
| 2016/0120609 A1* | 5/2016 | Jacobsen ............... A61B 5/062 600/424 |

OTHER PUBLICATIONS

Author: Anonymous, "MIKROE-1996", Mouser Electronics Inc. URL: https://www.mouser.de/datasheet/2/272/9dof-click-manual-v100-947706.pdf (Publication data: Dec. 31, 2015).

European Patent Office, Office Action issued for EP 17844277.8 (Sep. 11, 2020).

European Patent Office, Extended European Search Report for EP 17844277.8 (Aug. 31, 2020).

* cited by examiner

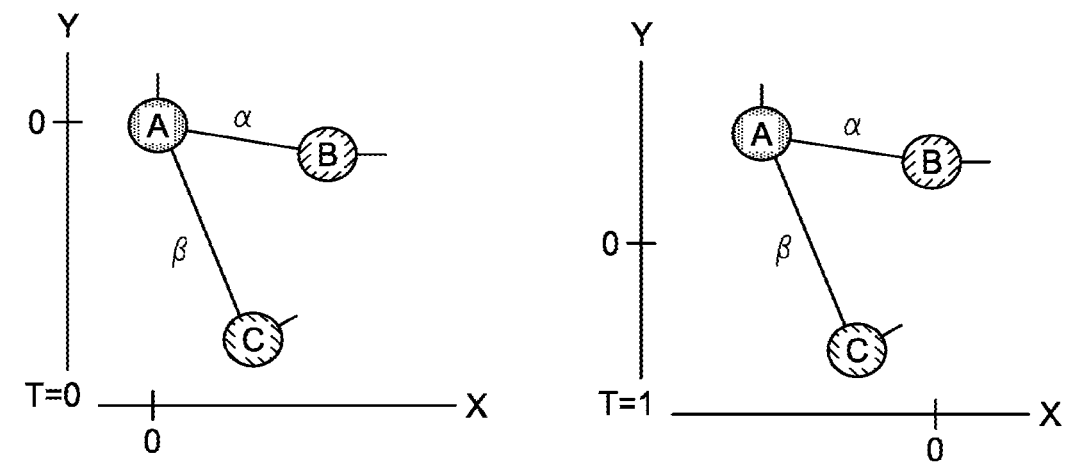
FIG. 14
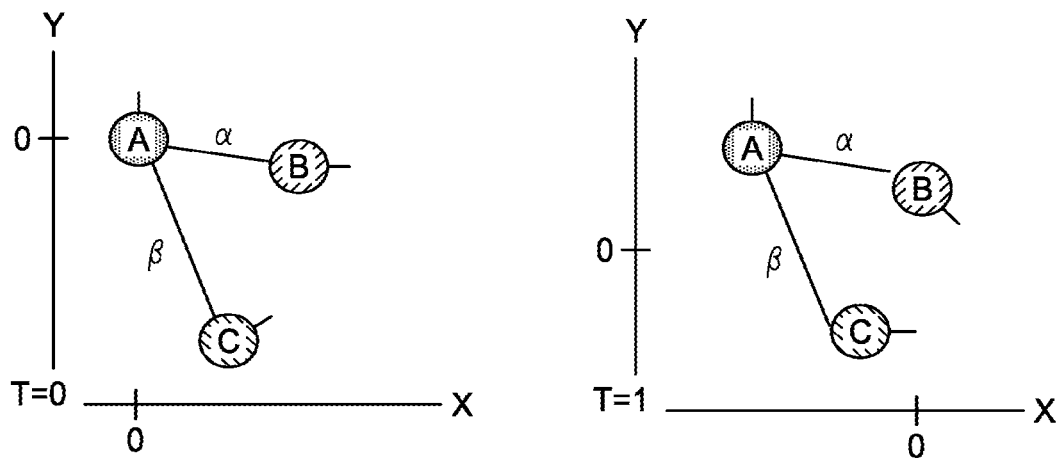
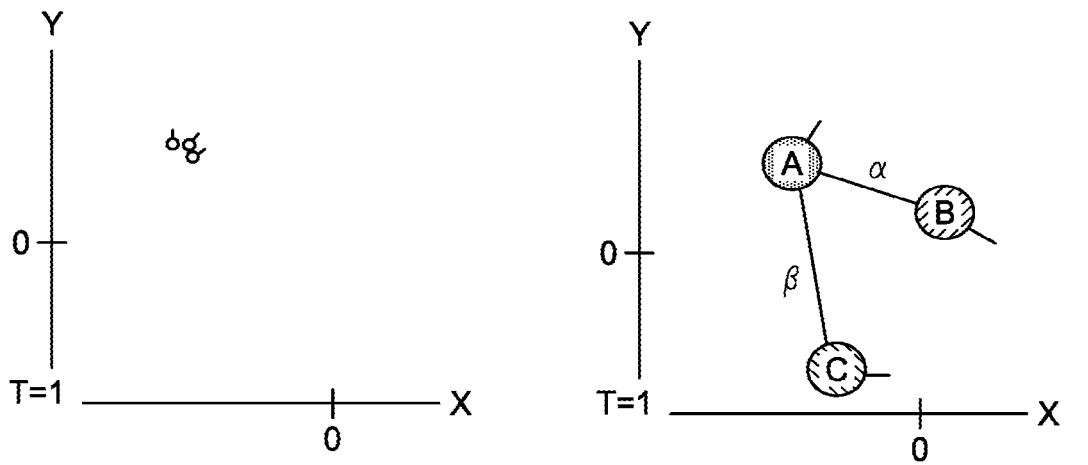
FIG. 15

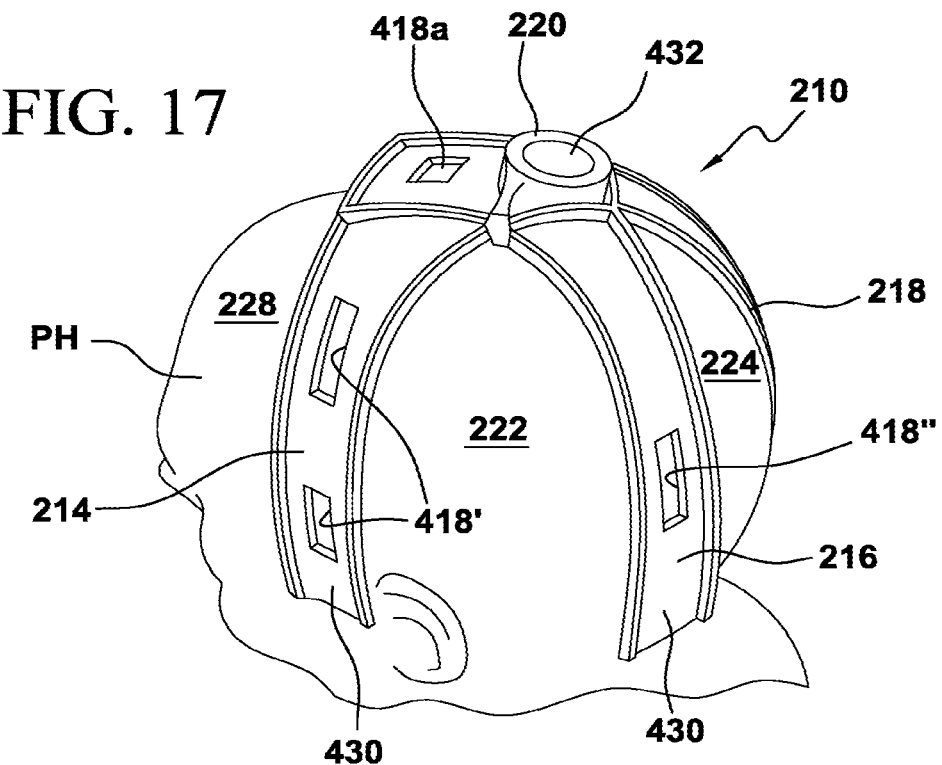

SYSTEM, DEVICES AND METHOD FOR SURGICAL NAVIGATION INCLUDING ACTIVE TRACKING AND DRIFT ELIMINATION

BACKGROUND OF THE INVENTION

The invention relates to surgical navigation systems for tracking surgical instruments within a subject's body during a surgical procedure to enable imaging of internal organs and surgical instruments relative to each other.

Surgical navigation systems have been devised that provide a graphic representation of surgical instruments relative to a patient's internal anatomy—particularly eloquent neurological structures such as the brain or spinal cord as they relate to nearby structures—displayed so-as-to inform surgeons during a procedure. These aforementioned surgical navigation systems map the position of the patient and thus the precise location of the parts of the body to be operatively treated in relation to the surgical instruments, keeping track of the instruments' positions and dimensions including operative tips and leading edges.

A typical surgical navigation system employs passive data collection with optical sensors. The setup includes a computer to which two or more external referencing cameras are connected. In such an arrangement these cameras in-essence, having an external line of site, map both (A) the position of artificial or natural landmarks affixed to a frame surrounding the patient sometimes supplemented with landmarks affixed to the patient for added accuracy as well as (B) the position of radiative emitters applied to the surgical instruments, or (C) radio opaque reflector affixed to the real coordinate system and the instruments.

The procedure starts with affixing a set of artificial landmarks upon the patient's anatomy, around the zone of interest that will be operatively treated. These landmarks are detected by the perioperative imaging and therefore provide points in a virtual coordinate system. These points can then be merged with defined points on the patient's anatomy acquired intraoperatively by the process of manual registration and correlated to the adjacent real coordinate system established by the radio opaque landmarks detected by the camera. Further, the emitter-detector array of the passive reflector system can be used to acquire real time surface topography and further define depth to the points in the surgical field being merged with the virtual representation of the same points. These points are identical to each other in physical properties. They are typically affixed to the patient by some form of adhesive plaster. This setup including the physical landmark adjacent to the patient detected by the camera, external landmarks, patient, and cameras is arranged appropriately within the operative suite, a process which may lead to difficulties acquiring real-time data.

The process of registering the external landmarks placed on the patient to the same external landmarks visualized on the CT or MRI map may be a time-consuming process in which the surgeon accesses each individual landmark on the patient with a pointer and assigns the landmark within the computer; the landmarks in the operating position correspond to those detected in the computer tomography. This process of registration requires that all landmarks need to be accessed a number of times, followed each time, by manually assigning their position to the computer tomography (CT) map. Utilizing the passive reflector system only allows registration of an instrument as a linear object based on acquisition of points and definition of a preset length and shape. While this process can allow for the tracking of orientation and position, due to the points for reference being separate from the instrument itself, this method cannot account for deformation of the instrument and can lead to increased error.

This is consistent with the system as set forth in U.S. Pat. No. 6,351,659; describing a neuro-navigation system that includes passive reflectors and markers—which vary in shape, size and material as well as arrangement or attachment on (A) the parts of the body/subject to be operatively treated and on (B) the surgical instruments. The system includes a source of infrared radiation, at least two mapping or referencing cameras, and a computer unit with a graphic display terminal connected to the cameras. At least two reflectors are provided which can be applied in a replaceable fashion via adapters to instruments or apparatus employed in the operation. Owing to a characteristic individual arrangement of the reflectors each surgical instrument reflects an image which can be sensed exclusively for the particular instrument concerned. The computer unit "recognizes" each individual instrument via the camera sensor and is able to display the position of its tip.

In older surgical navigation systems, two or more active emitters, emitting, for example, beams of infrared radiation, are applied to each instrument or operation apparatus and act as spot emitters located on a surface area. Within the instrument an electronic device is provided permitting emission of the signals, the instrument being connected at its rear end by a cable to the computer unit. From the emitted signals the computer unit is able to identify the position and subsequently extrapolate three-dimensional position of the instruments or the tips thereof.

This vintage instrument referencing system is also hampered by several drawbacks. Prior to the introduction of affordable microprocessors, the inclusion of electronic components made such instruments more expensive. In addition, the cables attaching the instrument to the computer unit were an obstruction to free movement and could obstruct operative treatment, especially if multiple instruments were used—as was often the case.

Active optical emitters attached as points to a surface area of the instrument can be "seen" only in the line of sight of the camera system. This restricted angular view proves to be impractical especially when considering that the source can easily be concealed by the instrument itself or by the hand of the surgeon interrupting the line of sight.

Neuro-navigation systems for neurosurgical operation were then improved; like previous systems they utilized real-time imaging in tandem with perioperative images but modified hardware in-order-to address the aforementioned difficulties regarding cables. This particular system afforded the operator the ability to visualize detailed anatomy based on MRI, CT, and possibly DTI imaging (depending on the modalities preferred by a particular hospital).

Regarding hardware improvements of existing technology, the current use of passive or reflective emitters allowed for the elimination of previously needed cable connection to the computer unit—these cables transmitted the information to the computer and supplied the "internal life"[1] of the electronic components within the instruments. Removing these cables gave the surgeon more freedom from obstruction and allowed for more liberated movement intraoperatively. However, in removing the "internal life"[1] of such instruments it precluded the design of the instruments as "electronic". This removed the idea that the instrument could include electronics and be the subject of future rational improvements; this may have, unintentionally, stagnated the improvement of this neuro-navigational technology—a concept revisited in improvements discussed herein.

[1]"Internal life" referring to electronic components within an instrument often requiring a power source.

Present surgical navigation systems exhibit (A) constant points of failure inherent to their design, (B) specific points of failure depending on the operation and operative approach, and (C) difficulties involved with setting up an operative field and operating room as a function of restrictions relevant to current software.

Constant points of failure, arising from design, include:
1) Difficulty with topographic resolution: pertaining both to topographic resolution of instruments and image renderings.
   a. Topographic resolution of instruments: given that an external camera is registering a passive emitter affixed to an instrument, surgical instruments are displayed as line segments and lack robust three-dimensional representation upon a virtual map. Therefore, topographic resolution of instruments themselves is non-existent in the present system with only a limited representation including but not limited to the behavior of the leading edge, angularity, and position in space.
   b. Topographic resolution and depth of surgical field: given that external cameras register the surface topography of the patients face and skull then indirectly extrapolate depth as a function of this surface topography this system again is only as accurate as the registration of surface topography. In concept This process would not seem to be implicated with error, but in practice has been a significant subject of difficulty in-so-far-as inaccurate extrapolation and therefore representation of true depth. A testament, to such limitations is infield experience with this system whereby instruments can appear to drift or not to align with the appropriate depth in real time from the image obtained perioperatively. These inaccuracies in navigation have led to a 2017 FDA recall of the BrainLab image-guided surgery system.
2) Difficulty with tracking hardware including $^{(A)}$the camera, $^{(B)}$its position reporting, and $^{(C)}$positioning the camera intraoperatively. The hardware is offered as either:
   a. An operative suite which requires construction of a new operating room with intricate planning and placement of hardware in permanent or semi mobile positions, or
   b. Mobile hardware in which the camera is on a mobile cart. The mobile cart camera was subject to governmental regulatory (FDA) recall several years ago for tracking difficulties in which insert position relative to the tracking hardware was lost making correlation to the topographic image infeasible.
3) Difficulty with tracking arising from instrumentation including the star tracking hardware system intraoperatively. The star tracking system requires a separate piece of hardware, "the star", which is three radio-opaque dense metal balls detected by the camera. They are positioned in the X, Y, and Z planes and translate their position above the field; the star is attached to either an instrument or a clamp. This attempts to account for the four dimensions of the operative field, X, Y, and Z values representing orientation, and depth. However, this requires exact positioning and distance in-order-to translate depth with accuracy. The instruments are also obstructive, bulky, and obfuscate the operative field. Also in specific instances if the appropriate distance and angle between two stars and the camera is not maintained this may perturb the angle between the camera and instrument causing the tracking position to be entirely lost.

Specific points of failure for intracranial, and endoscopic skull base, and spine surgery using the aforementioned passive neuro-navigation system hardware and software are as follows:
1) Difficulty accounting for brain shift in intracranial cases upon opening both the cranial vault and subsequently the meninges. Specific to intracranial operations, a stylet is used once the meninges have been reflected and the relative position of the brain to the bony anatomy has shifted due to the change in volume and pressure of the surrounding meninges and CSF flow. This method of using the cameras and the star tracking system in conjunction with the stylet for augmented tracking detail brings forth two subsequent problems.
   a. The star hardware is placed on the head clamp for intracranial cases and the stylet that is placed through a guide which is attached to said clamp. Tracking all of the instruments placed intracranially during the operation requires a star tracking device on the instrument and the tracking device on the clamp. Therefore use of instrumentation intraoperatively requires removal of the stylet and placement of an instrument, which leads to brain shift that is unaccounted for by the tracking system.
   b. Such removal of instruments or parenchyma over the course of an operation results in a change in volume of the brain, which leads to a change in relative position between the brain, the meninges in CSF, and the bony anatomy. To remedy the difficulties in shift that this results in, the neuro-navigation units are offered with intraoperative CT and MRI scanners. These are only offered with the operative suite. These allow one to obtain new operative imaging incorporating continued tracking information obtained via the camera and star tracking system which has the difficulties listed above. Moreover, depending on the construction of the operative suite, the camera may be limited in movement and the angles needed for the star tracking hardware may not be attainable, leading to disappearance of topographic resolution intraoperatively.
2) Difficulty orienting to changes in spine position following operative manipulation of bony elements resulting in destabilization of the previous orientation. Neuro-navigation of the spine also requires star tracking devices. The tracking devices are not only on handheld instruments but also on clamps placed at the level above or below the operative level of interest. Surgical correction of spinal deformity often requires destabilization of the spine caused by removal of bony architecture for the implementation of arthrodesis. Said destabilization of the spine can result in forward and backward translation, corrected intraoperatively by reduction. Loss of structural integrity in the body anatomy to which the star tracker is attached via the clamp can result in the following:
   a. Inaccurate merging of preoperative imaging with a newly translated unstable spinal level(s). This particular point is a major reason for the advent of intraoperative imaging including CT and MRI that necessitates the designing of an entire operative suite, an option that few users have. Alternatively, software algorithms that allow the approximation of new position with reorientation of the clamps intraoperatively exist. Both methods—the latter being less accurate—require significant delays in the operating room. Moreover, the CT and MRI machines require tracks to move on. These tracks in many cases have been placed in the way of the rotating camera arm for the mobile camera unit and lead to the inability to obtain the appropriate angle with pursuant loss of topographic resolution.

3) Difficulty in endoscopic skull base surgery owing to drift of apparent instrument location in real-time merging of instrument tracking data with perioperative imaging. This drift arises at least in part due to difficulty with topographic resolution obtained by translation approximation using star tracker on clamp.

The above system has been through multiple iterations of its hardware and multiple iterations of the software to remedy some of these tracking difficulties. The problems listed above develop from the fact that the tracking requires a hardware component mounted either on the head clamp or bony spinal architecture correlated with infrared sensing cameras. It is this triangulation platform that gives rise to the difficulty in position and topographic resolution listed. Moreover, these passive tracking systems do not employ direct position acquisition. These systems are limited to indirect acquisition of position based on construction of multiple coordinate systems and statistical regression analysis in merging with a virtual system. Whereas direct acquisition of position allows the construction and function within a single system directly measuring position from base characteristics.

The alternative to passive tracking is known as active tracking. While passive systems employ stationary markers that are typically identified by an external sensor, active tracking systems rely on sensors that measure the forces acting on the object and calculate the relative movement or change in orientation. These sensors are typically grouped together into a single integrated chip and are known collectively as inertial measurement units (IMUs). Active tracking using IMUs is not the same as active optical tracking used in vintage systems discussed above, as' the active optical system requires an external sensor for reference and derive position in part from a system dependent on line of sight, while the IMUs acquire position and orientation changes via dead reckoning. Dead reckoning is the process of determining an object's position by measuring the object's acceleration and velocity over an interval of time allowing derivation of position independent of line of site; thus, alleviating certain aspects of external reference technologies which translate to the most troublesome of aforementioned difficulties.

The introduction of IMUs into both advanced and commercially available technologies has allowed a user to calculate an object's position and orientation in real-time. The three most common sensors to measure pose, defined here as position and orientation within a fixed reference frame, within an IMU include an accelerometer, a gyroscope, and a magnetometer. The number and type of sensors found within each IMU varies depending on the product and manufacturer. Each IMU is typically denoted by the total number of degrees of freedom (DOFs) measured by the sensor. The accelerometer can measure one-to-three DOFs; one for each axis in the Cartesian coordinate system. The gyroscope can measure three DOFs: roll, pitch and yaw; as they relate to Euler angles. The magnetometer measures three more DOFs, also based within the Cartesian coordinate system.

Due to their small size, the sensors are referred to as micro-electrical-mechanical systems, or MEMS. While each sensor is measuring the same forces as their macroscopic counterparts, their method of data collection differs.

A MEMS-accelerometer is essentially a capacitor. Two sets of metal bars separate two capacitor terminals. A small mass is attached to the end of one set of bars. As the mass accelerates, inertia causes the relative position between the two sets of bars to change, resulting in a change in capacitance between the two terminals. This measurable signal is translated into a force in one of the Cartesian axes.

A MEMS-gyroscope utilizes the Coriolis Effect to measure angular velocity. The Coriolis Effect occurs when a mass moves in a rotating system, causing the mass to experience an additional force, the Coriolis force, orthogonal to both the movement and axis of rotation.

The MEMS-gyroscope measures change in capacitance in a similar fashion to the accelerometer. However, the entire capacitor system is set within an oscillating structure. When the system is rotated, a flexible portion within the oscillating system experiences the Coriolis force, and alters the capacitance. This measurable signal is translated into a change in one of the Euler angles in terms of angular velocity.

A MEMS-magnetometer is a small compass that generally utilizes the Hall Effect. When a current passes through a conductive plate, the current follows the path of least energy, which, when there is no interference, is a straight line. The presence of a magnetic field, however, will exert a force on the current; therefore, deflecting its path, causing one side of the plate to be negatively charged and the other to be positively charged. By measuring the charge differential, the strength of a magnetic field passing through that plane can be calculated.

Each of these sensors has its limitations and flaws. The magnetometer is capable of detecting any magnetic field. Each current within a microchip produces a magnetic field, which has the potential to disrupt the magnetometer. Generally, magnetic north is much stronger than the other forces. In practice, there is little to no interference and the magnetometer works accurately as magnetic north significantly overpowers interference from magnetic fields of subordinate magnitude. Of the three sensors, this is the most reliable. The gyroscope measures angular velocity and is inherently subject to error; this is due to noise. In-order-to calculate the Euler angle, the data must be integrated, effectively amplifying this inherent background noise to create a discordance between true position and that being calculated by the gyroscope, known as integration drift. The effects are small, but because integration via dead reckoning is inherently cumulative the summation of small respective inaccuracies amplified by integration accumulate over time, causing the readout to decrease in accuracy the longer the system is collecting data. In addition, the frequency of oscillation within the gyroscope must be unique within the device. If there are other units within the IMU emitting similar frequencies to that of the gyroscope, the oscillations will interfere with one another further implicating interference, subsequently amplified by integration—resulting in even, greater drift.

The accelerometer presents the greatest limitation of the three instruments comprising the IMU. These limitations include gravity and drift. The force of gravity is constantly effecting the sensor, causing the sensor to report a constant upward acceleration. This force can be removed simply by negating any constant upward force of 9.8 m/s²—the corresponding acceleration due to gravity. Unfortunately, this value is only an estimate that can change depending on one's position on the globe. Furthermore, changes in orientation complicate accurate negation of gravitational force as the force of gravity though constant must be negated as it is perceived through an infinite translation through different finite positions as perceived via the gyroscope—such as occurs in more complex maneuvers especially those that do not strictly constrain to one specific plane of movement on the Cartesian axes (X, Y, and Z) or transect multiple axes of movement. The slight differences in true gravitational acceleration as well as those implicated with changes in orientation lead to inaccuracies.

Worse, yet again, is drift. The accelerometer is collecting data describing the acceleration function. To calculate an object's position, the position function is required. To calculate the position function, the acceleration function must be integrated twice, first to velocity then once again to position—implicating amplification of this initial inaccuracy in a roughly exponential fashion. From a mathematical standpoint, these calculations can be done as follows:

$$a(t) = v'(t) = r''(t)$$

$$v(t) = \int a(t)dt = xt \mid c$$

$$r(t) \int v(t)dt = \frac{xt^2}{2} + c_1 t + c_2$$

From a practical standpoint, this is a significant challenge. To start, $C_1$ and $C_2$ cannot be determined without knowing more information about the system, e.g., true values of acceleration and velocity at some time, t.

Moreover, for a system that collects data points representing instantaneous acceleration, a function that describes the acceleration must be created. Unfortunately, all measurements have error; hence the calculated acceleration function will deviate from the true acceleration function. When a function is integrated, any errors are compounded. As-a-result, in existing graphical displays of the position, the object has a tendency to drift far off course; often in a short amount of time.

The most commonly applied method of correcting integration drift is to add an external sensor. An external sensor is a sensor separate from the IMU. For large scale systems, Global Positioning System (GPS) is often used as the external sensor. This would require access to satellite data via an internet connection. For small scale systems, a combination of emitter cameras and fiducials can usually be employed, similar to the optical tracking systems presently in use and previously discussed herein.

To elaborate, a fiducial, or marker, is placed somewhere in the system. An emitter shoots a particular wavelength of light that is reflected by the fiducial. A camera tracks the fiducial as the system evolves. While the IMU provides instantaneous data on the system, the data collected from the camera is analyzed and used to correct problems associated with the IMU. GPS is used in the same manner.

Maintaining a line of sight between the camera and the markers, or a solid connection in the case of the GPS, becomes paramount in these systems. Any interference between the camera and markers diminishes the accuracy between the IMU and the digital image—and inculcates a potential source of error.

Thus far, the correction of drift is developed on a case-by-case basis, with no generalized solution for all applications. However, the system henceforth disclosed could be applied to solve integration drift on any system without an external reference. A Self Referential Tracking System employs the use of multiple independent IMUs positioned around the head of a patient undergoing various forms of intracranial neurological surgery, as well as, in the instruments used for surgery. The goal being accurate patient registration, in which the patient's position and orientation in space can be described and matched with both a digital rendering of an MRI or CT image, and the instruments entering into the operative field.

Historically, two head clamps, the Mayfield and the Sugita, are used in neurosurgical applications. The Mayfield head clamp (1) is comprised of two forged metal or graphite, curved sliding arms. On the terminus of one arm (Arm 1) is a single pin with a pressure gauge. On the terminus of the other arm (Arm 2) are a plurality of rocker pins on an arch. The pins are applied with a pressure of 20-80 psi to secure the head clamp into the bone of the calvarium. The ideal pressure used to stabilize the head is 60-80 psi. The two curved arms are secured to each other through a ratchetting sliding mechanism wherein Arm 1 slides into Arm 2 and locks. The Mayfield head clamp is often used with the Layla-Yasargil retractor bar. The Sugita head clamp (2) is a six-point fixation system made from either forged metal or carbon fiber and has two curved arms seated in a center pivot. The two arms each have two pins that are placed through a respective arm. The Sugita headframe is accompanied by various adjunct pieces, including a plate for resting cottonoids, arms for retractors, and a second arch for retracting the skin and muscle flap.

As mentioned, the head clamp must stabilize the head during operative techniques. The techniques of interest include (I) drilling burr holes and (II) microsurgical manipulation of tissues. Drilling burr holes requires use of a hydraulic or electric drill with a perforating- or acorn-drill bit, the choice of which is left to surgeon preference. In either scenario, the drill set is capable of generating 75,000 RPM. The torque generated during drilling is resisted by several features of current headframe design. These include A) pinning to bone B) rigid materials with great tensile strength and elastic modulus, and C) thickness of the forged construct to resist bending. The Mayfield head clamp has an additional mechanism to resist these forces, rocker pins. Microsurgical manipulation specifically refers to development of tissue planes, dissection-of dura and arachnoid, entrance into the subarachnoid space, splitting of the falx cerebri and/or tentorium, and manipulation of nerves and blood vessels as in the application of aneurysm clips or the case of microvascular decompression. These commonly employed techniques require stabilization of the head restrictive to sub-millimeter movement.

The application of the head clamp and head frame is also a consideration. As the workflows are similar for both the Mayfield and the Sugita head clamps, they will be discussed together. The patient is first brought into the room on a stretcher. The patient is awake and may be asked to move to the operating table voluntarily. Alternatively, the patient may be induced by anesthesia and intubated on the stretcher prior to movement by the operating room (OR) team. Once the patient is asleep and intubated on the OR table, the operative area of interest is prepared such as in shaving hair which may be obstructive. The head of the bed is removed. The head of the patient is held in the proposed operative position by an assistant while the site(s) of insertion of the head clamp pins is prepared in a sterile fashion. The pin tips are prepared with a sterile antibiotic ointment. The clamp is then inserted by applying pressure to the opposing sides until it is seated percutaneously into the outer layer of the skull. Now, the pressure is adjusted to 60 psi, and the locking mechanism is engaged. The head clamp is secured to the head frame which is attached to the bed. The field is then prepared and draped in the usual fashion, which includes application of Ioban and paper drapes attached by adhesive.

The above head clamps are not approach specific. Further, in 2016, the FDA issued a communication regarding failures of the existing head clamps and associated complications. Complications include abscess formation due to pin introduction into the skull, fracture of the head clamp, skin lacerations, and injuries associated with patients' heads falling.

SUMMARY OF THE INVENTION

The present invention aims to provide improvements for surgical navigation systems, particularly a self-reporting system that does not require outside triangulation such as would be provided by communication between the hardware component and external camera(s). The system of the present invention acquires surface topography by referencing a point or points on the exterior surface of the patient anatomy via fiducials which it then uses to augment the real-time acquisition of topographic resolution for further spatial definition and depth.

The present invention provides apparatus and/or methodology for facilitating or improving accurate, real-time tracking of surgical instruments within a surgical operative field, so that instrument positions and orientations can be accurately overlaid onto, or correlated with, three dimensional renderings of the patient's internal organs, specifically the brain. The invention facilitates or improves accurate, real-time tracking of any set of objects within a pertinent field or space, so that relative positions and orientations of the objects can be accurately correlated.

More particularly, the present invention aims to provide surgical navigation componentry that ameliorates or compensates for potential sources of error such as gravity and integration drift in the use of motion sensor data for tracking changes in positions of surgical instruments relative to an operative site.

The present invention aims to provide an improved head clamp for neurosurgical applications, wherein the head clamp is approach specific and increases the safety of the patient, the efficiency of the surgeon, and the accuracy of the active tracking system as described herein.

The present invention is directed to improvements in surgical navigation systems for tracking surgical instruments and a subject body during a surgical procedure to enable imaging of internal organs and surgical instruments relative to each other using an active tracking system. An active tracking system as disclosed herein addresses points of failure associated with passive and optical tracking systems, described above. Modified surgical equipment pursuant to the invention increases the safety of the procedure and also provides the means by which an active tracking system can accurately measure position and orientation via dead reckoning in real-time.

Where movement of an inertial measurement unit (IMU) is calculated using numerical integration of the collected data, inaccuracies in the measurements result in integration drift. Identifying true or absolute movement in this scenario is not possible. Any movement is displayed relative to the arbitrary starting point of the IMU. There is only one frame of reference; that of the IMU.

Adding a fixed external sensor to the system introduces a new reference frame; moreover, it is fixed. The IMU provides more accurate data on instantaneous properties; the camera adds a frame of reference that constrains the data, providing the ability to check and alter the data. Now the movement of the IMU can be accurately identified within this reference frame.

Hence, in the absence of a camera, some constraint on the system must be introduced to check the data and calculations.

This system recognizes the need for an additional point of reference, and overcomes this need by the introduction of a virtual reference frame. Said virtual reference frame is constructed by the known characteristics of the system as well as the real-time digital measurements from the IMUs. The real-time digital measurements are also used to analyze the physical properties of the surrounding volume and formulate a second, more stable virtual frame of reference onto which the first, statistically generated reference frame, is situated.

The generation of local frames of reference and field maps necessitate the need for specialized equipment, including but not limited to a surgical head clamp in the case of neurosurgery.

The location of the operative target in intracranial neurosurgical cases determines the approach, that is, the access location on the skull and the directions of instrument insertion. The chosen approach then dictates the preparation of the surgical field. Stabilization of the head is a necessity for common operative techniques used in neurosurgery and is a key factor in the feasibility of a chosen approach. Thus, a head clamp, typically attached to the bed frame by a head frame, is used.

A neuro-navigation accessory system in accordance with the present invention comprises seven separate software- and hardware-components (1-7 below) which are programmed to work with existing neural navigational software, for instance, as in the system described above (prior art). The components include:

(1) Trackers
(2) Modified surgical instruments
(3) CT/MRI opaque fiducial(s)
(4) Surgical head clamps(s)
(5) Ready-to-use, surgery specific kits
(6) A Calibration Apparatus
(7) Magnetic Navigation
(8) Internal Reference Arrays (IRA)

Trackers:

Each tracker unit includes four devices, namely (a) an inertial measurement unit (IMU), (b) a wireless transmitter, (c) a microprocessor, and (d) a power supply. The (a) IMU is composed of a (i) gyroscope, (ii) accelerometer, and (iii) magnetometer. These sensors may have a variety of degrees of freedom (DOF), generally three DOFs are optimal per component, resulting in a 9-DOF IMU which records the forces required for the calculations of orientation and relative position using numerical integration methods and statistical filters which we will be referring to as directly acquired position. The wireless transmitter—short, medium, or long range—broadcasts data collected by the IMU in any variety of modalities in isolation or in combination including but not limited to radiofrequency (RF), WiFi, Bluetooth, or possibly infrared or ultraviolet. This aforementioned data is transmitted to a receiver in a nearby computer. Each tracker broadcasts at a unique frequency to be distinguishable by the receiving computer. The microprocessor coordinates the subunit interactions, and a battery power supply powers each tracker without the need for wired connection. The size and shape of each tracker unit will vary based on the individual components used, however, custom circuit boards could reduce the volume. The subunits or component devices within each tracker work in tandem to transmit real-time positioning data to a receiver in a nearby computer.

These external trackers serve as external landmarks (digital and physical) which enable (A) the overlap or superposition of the surgical area of interest onto its corresponding surgical map, and (B) serve as a means by which the instruments can be tracked as an extension of their movement relative to this external frame of reference (often established by multiple external trackers/landmarks). The external trackers transmit information regarding changes in head positioning and orientation to the computer for processing. A single reference tracker may serve as a reference tracker to re-calibrate instruments to refresh the frame of reference if required.

The subunits or component devices of each tracker vary in construction or arrangement based on the surgery at hand. If only superficial attachment of trackers is needed, the subunit components may be wired together and housed within any variety of housing materials including plastic polymers, other materials of durable and or pliable construction to then be placed upon their specified relative locations. Alternatively, these tracker(s) may be placed upon the subject via multiple fiducials, surgical clamp(s), or in any plurality upon both the subject and surgical clamp(s) in a variety of combinations or embedded within surgical equipment. If, for example, trackers are embedded intimately within the construction of other external surgical equipment (for example, a surgical clamp) their individual subunit components may be present in any variety of arrangements within the ultrastructure of this piece of surgical equipment. For example, four trackers placed within a head clamp may only require one power supply, transmitter, and processor wired together but existing anywhere throughout the entire location of the head clamp itself.

Modified Surgical Instruments:

The modified surgical instruments pursuant to the present invention are made in a novel process involving the construction of a polymer core to provide the general shape of the instrument, and the deposition of a sturdy external layer to provide structural integrity necessary for operative strain—further, different materials can be employed in order to alter the properties of these instruments (in combination or in isolation) so as to embody characteristics more appropriate for either other operations/approaches or as an improvement to their existing properties so as to rationally enhance their design or address future difficulties alleviated by such an alteration in construction. Each instrument contains an area for which to house the IMUs; this area is often hollow and housed toward the core of the instrument—for purposes of insulating the technology—but does not necessarily need to be restricted to these characteristics.

The modified surgical instruments pursuant to the present invention each contain a tracking system preferably comprising a plurality of trackers disposed at predetermined mutually spaced locations on or within the respective instrument. These instrument trackers are similar in design to the trackers suitable for external landmarks or surgical clamps. The tracking systems are each composed of (a) the trackers, each comprising three IMUs, (b) a short range wireless transmitter, (c) a digital processor, and (d) a battery power supply. The three IMUs each include subcomponents of (i) an accelerometer, (ii) a gyroscope, and (iii) a magnetometer. The relative position and orientation of each IMU may vary in construction or arrangement based on the respective instrument and requirements of the system. The short range wireless transmitter broadcasts data collected by the IMUs at a unique frequency in any variety of modalities in isolation or in combination including but not limited to radiofrequency or RF, WiFi, Bluetooth, or possibly infrared or IR or ultraviolet or UV to a receiver in, or connected to, a nearby computer. The processor coordinates subunit interactions within each instrument. Alternate versions designed for instruments with an existing power cord or pneumatic line can omit the short range transmitter and the battery power supply. Instruments that undergo shape changes may require the introduction of an additional sensor, or unique circuitry to recognize conformation changes or deformational changes resultant from strain. Instruments that have multiple relatively moving parts may incorporate a set of IMUs for each part.

The trackers in the instruments differ from the trackers on external landmarks or surgical clamps; they not only contain a plurality of IMUs per tracker but also require unique data processing:

I. The software recognizes the instruments and applies different processing protocols for eliminating drift to within acceptable ranges and orientation and in doing so accurately display their directly acquired position.

II. The computer in concert with technology embedded within the instruments will account for adaptive properties of the instrument including
 a. Articulation behavior and conformation changes
 b. Acceptable deformation during the operation
 c. Unacceptable deformation during the operation (this includes compromised
 structural integrity).

III. For-the-purpose of simplifying final surgical counts the individual frequencies of the instruments can all be registered instantaneously by the receiver within the computer—a quick way to indicate that no instrument within the surgical kit is within the patient at the end of the operation.

CT/MRI Opaque Fiducial(s)

The CT/MRI opaque fiducial(s) as utilized pursuant to the present invention act to provide a fixed reference point by which the image for the CT/MRI can then be aligned. Preferably, the fiducial(s) are each in the shape of a trapezoidal prism with a depression on a top face. At the base of the depression is a thin layer of scan-opaque material which can be detected by a CT or MRI machine. A bottom face of the fiducial is coated with an adhesive. Each fiducial has a footprint of ~1 $cm^2$ and a height of ~2-3 mm. The dimensions of the scan-opaque material are fixed and known, such that software present in the primary computational terminal can detect and recreate each fiducial into a 3D digital space with relative positions and orientations matching physical structure.

Surgical Head Clamps(s)

A device for fixing a patient's head for a neurosurgical procedure, henceforth referred to as the "head clamp", comprises, in accordance with the present invention, a (4a) superstructure, a plurality of (4b) head contact members, (4c) dampeners, and a (4d) 'connector column'.

The superstructure of the head clamp is a substantially rigid frame including a plurality of arcuate arms arranged in a predetermined configuration adapted to a particular neurosurgical approach. The arms are connected to one another at a hub region and are curved as to fit around the superior half of a patient's head. The arms are arranged to expose the area of surgical approach offered for a variety of known surgical approaches, the utilization of a specific clamp is left to surgeon preference.

A crossbeam is found opposite the approach site located between two adjacent arms. The crossbeam is similar in design the arms in that it is made of the same material and has similar dimensions. It connects the two arms perpendicularly. In the center of the crossbeam is a hole extending through the body of this crossbeam.

On the superior aspect of the superstructure, at the hub region, is a hemispherical cavity. Along the external edge of this cavity is an external thread. The cavity serves as the socket for a ball-and-socket joint used to secure the head clamp of the bed via a head frame designed specifically for this system. A ring with an internal thread interlocks with the external thread to apply a force against the ball within the socket or hemispherical cavity, thereby preventing movement of the head clamp relative to the bed but allowing for relatively unrestricted rotational motion.

According to a further feature of the present invention, the arms of the frame each include a central body portion having longitudinal edges and further include at least two flanges extending from the longitudinal edges perpendicularly to the portion of the central body. This feature serves to reinforce the arms, as rigidity is a desirable characteristic.

According to an additional feature of the present invention, the arms each include a superstructure made of hard and sturdy material. The present design includes but is not limited to a durable polymer; for example alternative compositions could be utilized such as amalgams, metals, various molecular structures or isomers of present materials. Each of the arms are coated on an interior or concave side with a layer of resilient material.

The head clamp described herein comes in multiple designs and configurations to accommodate the surgical approach. While the general properties of the (4a) superstructure and the head clamp components (4b-d) remain unvarying between designs, the shape of the superstructure and the positions of each arm relative to the patient's head vary.

In a first specific embodiment of the present invention there are two anterior arms configured to extend laterally opposite one another anterior to the ears of the patient and two posterior arms angled with respect to one another for extending down the back of the patient's head at approximately forty-five degrees equidistant from the midsagittal plane of the patient. The crossbeam extends between the latter. This embodiment is formed for use in a bifrontal coronal craniotomy. Typically, the two anterior arms are disposed in a common plane. The arms then collectively define four gaps or inter-arm spaces including three on one side of the common plane and one on an opposite side of the common plane.

In a second specific embodiment of the present invention, there are two anterior arms angled with respect to one another and configured to extend down over the patient's forehead in vertical alignment with the eyes of the patient and two posterior arms angled with respect to one another and configured to extend down over the occipital region of the patient's head. The arms of this second embodiment further include an additional arm configured to extend laterally and anterior to an ear of the patient. The crossbeam is located between the additional arm and adjacent posterior arm. This embodiment is adapted for use in a pteryonal craniotomy.

The arms of the second embodiment may collectively define five gaps or inter-arm spaces between adjacent arms, one of the gaps or inter-arm spaces subtending an angle of greater than 90 degrees and each of the other gaps or inter-arm spaces subtending an angle of less than ninety degrees. The largest gap or inter-arm space is disposed between one of the two anterior arms and one of the two posterior arms.

Alternatively, the arms of the second embodiment may collectively define five gaps or inter-arm spaces between adjacent arms, with two of the gaps or inter-arm spaces each subtending an angle of greater than 90 degrees. In that case, each of the other three gaps or inter-arm spaces subtend an angle of less than ninety degrees. One of the ninety-degree-plus gaps or inter-arm spaces is disposed between one of the two anterior arms and one of the two posterior arms, while the other ninety-degree-plus gap or inter-arm space is disposed between the additional arm and the other of the two posterior arms. This modification to the second embodiment is adapted for use in a combined pteryonal-retrosigmoid approach.

In a third specific embodiment of the present invention, there are two anterior arms each configured to extend laterally and anterior to a respective ear of the patient and an additional anterior arm configured to extend down over the patient's forehead in vertical alignment with the bridge of the patient's nose. In this third embodiment two posterior arms are angled with respect to one another and configured to extend down on one side of the patient's head posterior to one of the patient's ears. The crossbeam is located between the adjacent lateral and posterior arms. This embodiment is adapted for use in a retrosigmoid craniotomy.

The arms of this third specific embodiment collectively define five gaps or inter-arm spaces between adjacent arms. Specifically, two of the gaps or inter-arm spaces may each subtend an angle of greater than 90 degrees, while each of the other three gaps or inter-arm spaces subtend an angle of less than 90 degrees. One of the gaps or inter-arm spaces subtending an angle of greater than 90 degrees is typically disposed between one of the two anterior arms and one of the two posterior arms, while the other gap or inter-arm space subtending an angle of greater than 90 degrees is disposed between the additional arm and the other of the two anterior arms.

Each of the arms is provided at a free end with a respective (4b) head contact member and (4c) dampener. The head contact member has an arcuate body and a plurality of ends or corners. The head contact member is configured so that the ends or corners are disposable in contact with the patient's head while the body of the contact member remains spaced from the same.

Pursuant to another feature of the present invention, the arcuate body is a plate in the form of a spherical section having at least three ends or corners. The head contact member is configured so that at least three ends or corners are disposable in contact with the patient's head while a major portion of the plate remains spaced from the patient. Preferably, the spherical section has four corners or points and is in a shape formed by a projection of a square onto a sphere such that a normal vector at a centroid of the square equals a normal vector of the sphere.

Preferably, the head contact member is connected in a pivotable manner to the free end of the respective one of the arms. The head contact member may be connected to the free end of the respective one of the arms via a coupling, configured to adjust a distance between the head contact member and the free end of the respective one of the arms.

The coupling component may include an elongate element movably connected to the free end of the respective one of the arms. The elongated element may take the particular form of a screw or threaded pin that traverses a threaded hole in the free end of the respective one of the arms.

Located between the coupling component and the arm of the superstructure is a (4c) dampener. This dampener is in the shape of a ring and could be composed of rubber or some similarly soft material. The dampener is designed to absorb vibrational energy generated by the application of surgical tool, against the patient in an effort to reduce the transfer of said vibrational energy to the superstructure of the head clamp.

Located on the exterior aspect of the (4a) superstructure are a plurality of cavities. These cavities allow for the insertion of a single (1) tracker at a specific angle. Both tracker and cavity are designed to ensure that only one orientation can be achieved.

The cavities are designed such that normal vectors projected from the center of the bottom faces of each of the cavities converge upon a single focal point. In this way; the relative positions and orientations of the trackers are known. Alternatively, the trackers fit in such a Way that their normal vectors are arbitrary, but known and specific to the design of the selected surgical head clamp variety.

This arbitrary frame of reference formed by tracker(s) on the head clamp can define the origin at the focal point or at some defined primary reference tracker located on the clamp. Other objects being tracked in the system, namely the surgical instrument fitted with trackers, utilize the frame of reference created by the trackers on the head clamp and the origin selected.

Located in said hole in said crossbeam is a cylindrical object, referred to here as a (4d) connector column, of diameter equal to that of the hole. Edges found on the connection column both above and below the portion that passes through the hole restrict the movement of the connector column so the object can rotate within the hole found in the crossbeam.

The majority of the body of this connection column is found on the interior space formed by the body of the head clamp. Only a small portion that makes up the edge that locks the connection column on to the cross beam extends in to the exterior space formed by the head clamp.

The interior portion of the connection column transitions from cylindrical to rectangular, such that the cross section of the terminus is a square. The cylindrical end is solid, while the rectangular end is hollow. Within the hollow section are two prongs that extend just beyond the end of the connection column. The connection column acts as the connection between the head clamp and the (3) fiducial. The said prongs act as the locking mechanism that fit into the cavity within the walls of the fiducial.

In addition, the point of contact with the patient that contains the fiducial is known. Using the relative orientations of the fiducials, the focal point, and all of the trackers, a 3D digital image can be overlaid into the digital frame of reference created by the set of trackers on the head clamp.

An alternate design to the tracker cavities is presented here. In this design the cavities extend through the arms of the superstructure. These cavities are larger such that a tracker can take a variety of positions and orientation extending through the arms. Using this design a plurality of the fiducials equal in number to the trackers, are positioned on the head of the patient in positioned near the cavities of the selected head clamp variety. The tracker casing would then be designed to interlock with the fiducials and extend through the head clamp. This design negates the need for the crossbeam and connection column. It moves the reference frame generated by the trackers from their fixed positions on the head clamp, to the honey architecture of the patient.

Ready-to-Use Surgery Specific Kits

Pursuant to the present invention, the system is intended to be presented as a ready-to-use, surgery specific kit. Each kit contains (A) trackers, (B) a specific combination of modified surgical tools tailored to the procedure being done, (C) a calibration sensor, and (D) a built in power supply. The fiducial(s) used for imaging of a surgical site or patient are provided separately and are not necessarily included in the kit. A surgery specific head clamp may be provided as well, though is not necessarily contained in the ready-to-use kit.

The layout of the kit is also used for calibration. The relative initial positions of every tracker and instrument is preprogrammed into the software and precisely matches the place holders within the kit. The instruments begin transmitting data to the main computer, after being activated either manually via a button or switch found on each instrument, or automatically via a single button or switch located in or on the kit that signals and activates all instruments at once. This initial position(s) of the tracker(s) placed on the head clamp can be confirmed in this way, as well; however, their positions and orientations are synched with the primary computer again after being attached to the head clamp. If removal of the trackers from the head clamp is required at any point during the operation—for intraoperative imaging perhaps—the trackers can be unclipped from the head clamp and returned to their starting positions within the kit; as can the instruments. Fiducials and head clamp remain fixed to the patient.

Accordingly, a surgical accessory kit in accordance with the present invention comprises a container and a plurality of electronic tracking devices removably disposed in the container. Each of the tracking devices occupies a predetermined location in the container. Each of the tracking devices includes a casing and a plurality of motion sensors, a power source, a signal transmitter, and a microprocessor all inside the casing. The motion sensors typically include gyroscopic elements, accelerometers, and/or magnetometer. The kit preferably further comprises one or more surgical instruments disposed in a predetermined position and orientation in the container, the surgical instruments each including a respective tracking device having a plurality of motion sensors, a power source, a signal transmitter, and a microprocessor all inside the respective surgical instrument (e.g., in the handle thereof). The system is further comprised of a calibration sensor containing a plurality of motion sensors, a power source, a signal transmitter, and a microprocessor.

Calibration Apparatus

The (C) calibration apparatus contains a 3-DOF calibration magnetometer and 3-DOF calibration accelerometer, microcontroller, power supply and wired or wireless transmitter. The calibration magnetometer can be incorporated into the kit or provided as a separate calibration apparatus. The calibration apparatus must be located on a level surface adjacent the operating table. All sensors transmit data to a central computer. This calibration apparatus is required for the navigation protocol or method described herein. Within this apparatus, the calibration sensors are moved automatically and in a controlled fashion, on tracks built into the kit, for example. Data is collected that can be used to identify and map the volume in which the trackers operate. The process is known as mobile calibration.

Magnetic Navigation

A method for use in tracking the position of an object in a given spatial region, comprises, in accordance with the present invention, providing a calibration apparatus and disposing the calibration apparatus in a predetermined orientation in the spatial region, the disposing of the calibration apparatus including monitoring the orientation with a calibration accelerometer. The method further comprises operating the calibration apparatus in a static calibration process to confirm that a local magnetic field in the spatial region is static and, while maintaining the calibration magnetometer in a stationary position, determining a direction for the strongest magnetic field in the spatial region. One determines from measurements of the calibration apparatus the position for strongest magnetic field. Upon determining the direction of a strongest magnetic field in the spatial region, one operates the calibration apparatus in a mobile calibration process to determine a 3D vector field map describing a magnetic vector as a function of position within at least a portion of the spatial region. Operating the calibration apparatus in a mobile calibration process comprises moving the calibration sensor along a predetermined path within the spatial region at a controlled rate while tracking acceleration and position of the calibration sensor as a function of time.

Pursuant to a feature of the invention, the moving of the calibration sensor along the predetermined path includes operating a robotic arm with a distal end holding the calibration sensor, or some mechanical apparatus comprising motors that control the movement of the sensor along the predetermined path.

The operating of the computer to construct a three-dimensional vector field may include executing extrapolation calculations to determine magnetic vectors at points in the vector field outside an area or direct measurement by the calibration sensor.

The computer may be operated to receive magnetic vector data from the calibration sensor and to construct a three-dimensional vector field mapping magnetic vectors as a function of position.

This method also includes the ability to detect (1) fluctuations in the magnetic field and (2) movement of the calibration apparatus both of which may be necessary for re-calibration in which case the user would then be notified that recalibration is necessary.

Internal Reference Arrays (IRA)

A surgical procedure pursuant to the present invention utilizes a newly formed mathematical constraint referred to here as an Internal Reference Array (IRA).

The present method applies to systems with multiple IMUs which are separated by known distances and orientations to each other. For example, consider a system in which there are two IMUs attached to opposite ends of a rigid bar. The relative vector between the two IMUs can be used as a constraint on the system. Once again, the IMUs are moved through space and data is collected. In this system, the movement of both IMUs over each interval of time can be observed. The relative vector between the two IMUs can be calculated; the difference between this measurement and the known constraint can be interpreted as drift.

It cannot be said that we have created an external frame of reference. Rather, we have two reference frames each, positioned in a known array, with an associated error between the two. Hence, the system may be called an Internal Reference Array (IRA).

All calculations coordinating the data from the sensors are now concerned with locating the true position and orientation of the sensor-bar system. Since both IMUs are collecting data, the calculated drift cannot be attributed to just one IMU. The error is distributed between the two sensors. Hence the most probable position and orientation can be calculated from the two sets of data, knowing that there is some error associated with this measurement.

Statistically, one way to decrease the error associated with any system is to increase the size of the population. Consider a system with many IMUs arranged into an array of known relative vectors. When any movement is made, the constraint allows one to see how the IMUs deviated from one another. Using statistics, the most probable position and orientation of the array as-a-whole can be calculated with these erroneous reported displacements referenced against the constraint and corrected.

There are two types of IRAs that are used in this system. The first is an array formed by trackers that are located about the patient's head, or set into cavities (either in the operating room or at the manufacturing facility) located on the exterior of the head clamp. This array is made up of five to seven separate trackers. In this array, the exact relative positions and orientations of each tracker is determined via CT/MRI imaging, or the physical design of the head clamp, as the trackers are locked into a fixed position relative to fiducial(s)/head clamp attached to the head of a patient PT—this is the constraint that is applied to the incoming data of this array. Only one array of this type is present in the present position monitoring system.

A second type of internal reference array is the array found within each modified surgical instrument contained within a given kit. Unlike the other type of array, which is made up of separate trackers, these arrays are made up of sensing devices that are integrated within the structure of the instrument but distributed throughout the instrument itself. The relative position and orientation of each sensor on the respective instrument is determined by the instrument's design and manufacturing process; this is the constraint that is applied to the incoming data of the arrays; put in another way the shape of the instrument itself houses the trackers with relative distances from one another that are absolute and thus act as constraints; therefore, the data reported that violates these fundamental properties can be eliminated so as to eliminate the adulteration of the data—this further enhances accuracy by utilizing the concept of an array. These physical constraints provide the basis for the elimination of drift and the accurate use of dead reckoning position and orientation acquisition. An IRA is present in every surgical instrument within the kit.

Application:

Depending on the type of surgery, a specific matching kit is selected that includes a dedicated or unique tracker or array of trackers and modified instruments. A surgery specific clamp is also provided.

Fiducial(s) are adhered to the head of the patient in a location consistent with the surgical approach. Alternatively, an array of fiducials is adhered to the face of the patient in such a way so-as-to provide topographical reference points. The patient receives a CT/MRI scan, and the neuro-navigation software produces a 3D model in which the position and orientation of the fiducial(s) are clearly detected.

The head clamp is then lined with the fiducials and the connection is made at the terminal end of the connection column. The locking mechanism found in the hollow space of the column prevents the head clamp from changing its position relative to the head clamp.

Once locked into the fiducial, the pins on the arms of the head clamp are turned and the head clamp becomes fixed to the patient's head. The head clamp is designed to rotate about the connection column given the design of the crossbeam. This allows for some "wiggle room" when applying the fiducial(s). Therefore, the distance of the head clamp to the fiducial is fixed but the angle may vary. Once the pins are turned and the head clamp is secured to the head, relational movement will be prevented. The cylindrical end of the connection column located on the exterior side of the crossbeam has tick marks representing degrees displayed on its exterior face. A single line is etched into the crossbeam. By observing which tick mark the face of the connection column lines up with in-regard-to the reference mark located on the crossbeam, the relative angle between the fiducial and the head clamp can be measured.

At this point, the trackers and instruments within the kit are activated and synced with the computer, generating and transmitting information concerning position to the computer.

Each tracker is clipped onto its corresponding position on the head clamp—if not already embedded within the surgical equipment within the kit. Since the final position of the trackers is in a predetermine location on the head clamp, the CT/MRI image can be synced with the trackers using the fiducial(s) as reference, and registration is complete. The distance and the angle of rotation between the fiducial and the head clamp are known. The restive position and orientation between the head clamp and trackers is known. Therefore, the relative position between the fiducial and trackers is known and fixed.

The data from all trackers is interpreted and coordinated with the existing neuro-navigation software by a receiver connected to a primary system computer located within the room. The array of trackers on the patient's head, found embedded into the head clamp at specific locations or combined individually with fiducials, transmits real-time positioning data and provides real-time image registration using the fiducial(s) to ensure proper alinement. The computer also processes all information from the trackers embedded in the instruments creating a virtual model of the instrument and overlaying it into the CT/MRI data and virtual frame of reference created by the array of trackers on the head clamp or head—as is consistent with existing technology—to create a map illustrating the position and orientation of the instruments.

The surgery is performed using the modified instruments. Due to the trackers, their positions within (and outside) the patient's head are known and are continuously tracked so that the positions and orientations of the instruments relative to the patient or subject are updated in real time.

Periodic recalibration of the instrument may be required after prolonged movement to ensure that the position of the instrument matches with the frame of reference created by the array of trackers on the head clamp. One tracker within the array will be designated the primary reference tracker. The instrument(s) in use will be placed in a specific position relative to this primary reference tracker, either by use of a groove or of a cavity into which the instrument can be oriented uniquely. A button or switch found on the instrument can be pressed, transmitting a signal to the main computer, resynching the digital representations of the instrument(s) and the primary reference tracker; thus, the head clamp and patient as well.

In the event of an intraoperative image the trackers are removed from the head clamp and returned to the kit. The head clamp and fiducial(s) remain on the patient. Once the new image is compiled and a digital version is made on the computer, calibration should be performed again. Afterwards, the trackers can be returned to their proper location on the head clamp, and the surgery can resume.

Upon completion of the surgery, the trackers, instrument, kit, fiducials, and head clamp can be removed and disposed of appropriately.

BRIEF DESCRIPTION OF THE DRAWINGS

FIGS. 10-15 are diagrams illustrating various configurations of MEMS type motion sensors, to explain an internal reference frame system for monitoring the motions of one or more bodies such as surgical instruments in a surgical navigation system, pursuant to the present invention.

FIG. 17 is a left, top and rear side perspective view of a first embodiment of a cranial fixation device in accordance with the present invention, configured for full coronal craniotomy, showing the device in position on a subject, the fixation device being utilization in a neurosurgical operation with surgical navigation as described herein.

FIG. 18 is a top plan view of the cranial fixation device of FIG. 17.

DETAILED DESCRIPTION

A surgical navigation system optimally includes motion sensors for tracking the location of a patient or a portion thereof, motion sensors in each surgical instrument for tracking the positions and orientations of the surgical instruments, and preferably a calibration sensor for detecting and measuring a magnetic field (magnitude and direction) in a portion of an operating room about an operating table for use as an external reference frame with which to determine the positions of the patient and the instruments relative to one another. With the use of a magnetic vector field as an external reference, the patient and instrument sensors include magnetometers for gauging position relative to the detected magnetic field. The system, particularly the instrument tracking sensors, may include multiple sensors with known relative positions to serve as internal reference arrays (IRAs) for minimizing, if not eliminating, computational drift.

The IRAs and the use of a magnetic field as an external reference facilitate and improve accurate, real-time, tracking of surgical instruments within a surgical operative field, relative to a surgical site on a patient, so that the instruments position and orientation can accurately be overlaid onto, or correlated with, three-dimensional renderings on a display or monitor of the patient's internal organs, specifically the brain. In the case of neurosurgery, a further improvement in accuracy of display imaging resides in the design of a head clamp. The various components disclosed herein, including the IRAs and magnetic field determination enable accurate, real-time, tracking of any set of objects within a pertinent field or space, so that relative positions and orientations of objects can accurately be correlated. The surgical navigation componentry of the present design ameliorates sources of error attributed to conventional determination of position via dead reckoning and through these innovations contribute to enhanced accuracy; so as to make positioning of surgical instruments relative to an operative site a more pragmatic endeavor in surgical operation moving forward.

As discussed in detail hereinafter, a neuro-navigation accessory system comprises: motion trackers for patient position monitoring, modified surgical instruments with motion trackers for sensing instrument movement, optional CT/MRI opaque fiducial(s) and/or surgical clamps for attachment of patient trackers, and calibration apparatus for magnetic navigation. These components may be provided in ready-to-use, surgery specific kits. Internal reference arrays (IRAs) are also preferably provided.

Figure 2:
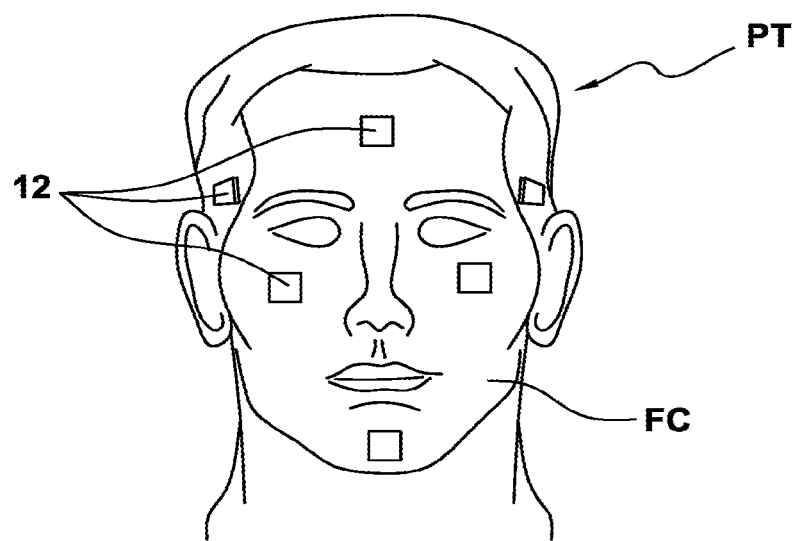
FIG. 2 is a schematic front elevational view of a human face, showing placement thereon of a plurality of fiducials as shown in FIG. 1.

There are two types of IRAs that are used in this system. The first is an array formed by pose trackers 18 (FIG. 3) adhered to the patient's head (FIG. 2). This array is made up of five-to-seven separate trackers 18. Each tracker 18 in this array includes an accelerometer 24a measuring 3-DOF, a gyroscope 24b measuring 3-DOF, and a magnetometer 24c measuring 3-DOF; a microprocessor 28; a wireless transmitter 26; and a power supply or battery 30. In this array, the exact relative pose of each tracker 18 is determined via CT/MRI imaging, as the trackers 18 are locked into a fixed position relative to fiducials 12 attached to the head of a patient PT; this is the constraint applied to the incoming data of the array (in concert with concepts previously discussed). Only one array of this type is present in the present position monitoring system.

An alternative version of this first array is formed by the pose trackers 18 that are locked into a cavity on the exterior of the surgery specific head clamp. This array is made up of five-to-seven separate trackers 18. Each tracker 18 in this array includes an accelerometer 24a measuring 3-DOF, a gyroscope 24b measuring 3-DOF, and a magnetometer 24c measuring 3-DOF; a microprocessor 28; a wireless transmitter 26; and a power supply or battery 30. In this array, the exact relative position of each tracker 18 is determined via CT/MRI imaging, as the trackers 18 are each locked into a fixed position relative to the head clamp, which is attached to the head of a patient PT. The relative position of the head clamp to the patient is known, as a portion of the head clamp is attached to a fiducial 12, located on the patient's head and observed via CT/MRI imaging (see FIGS. 24 and 25 and associated description).

Figure 4:
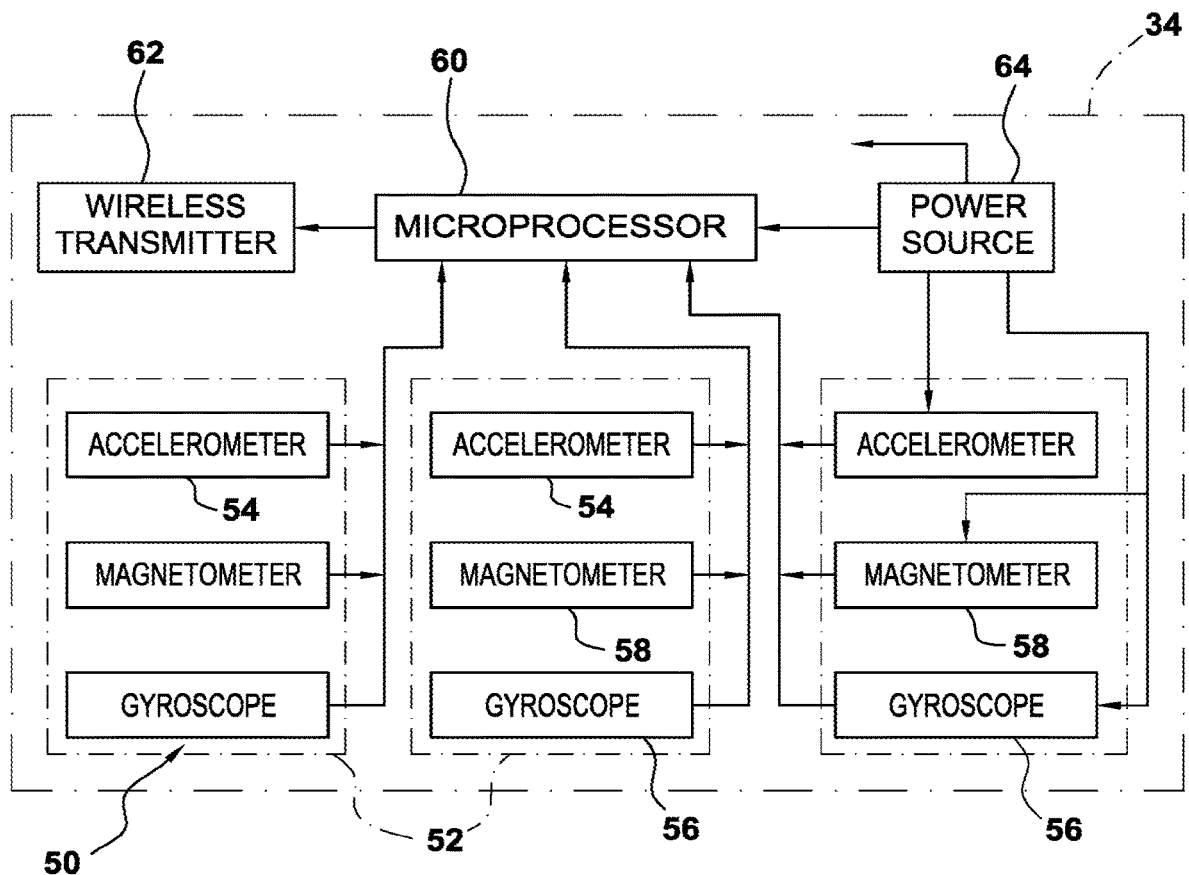
FIG. 4 is a block diagram of an object such as a surgical instrument pursuant to the present invention, showing multiple position and orientation inertial sensing devices for determination of the object's position and orientation so as to eliminate drift effects in the calculations.
Figure 5:
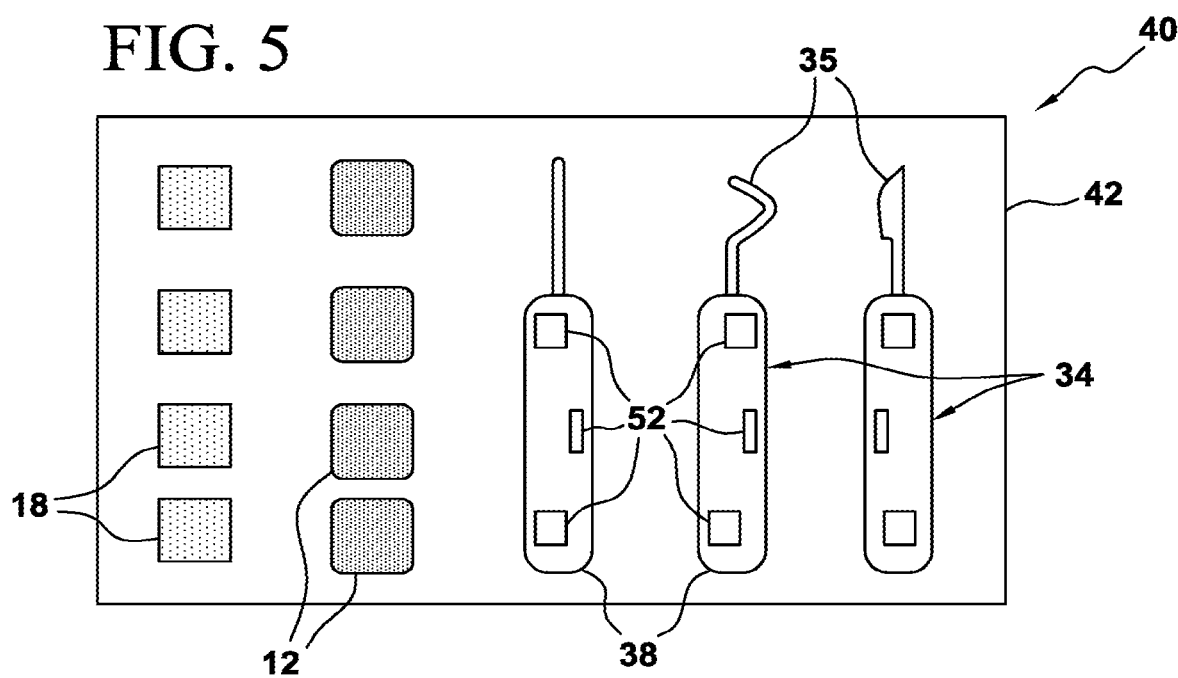
FIG. 5 is a schematic top plan view of a kit in accordance with the present invention, for use in a surgical navigation system in accordance with the invention.

A second type of IRA 50 is found within each instrument 34 (FIG. 4) within a kit 40 (FIG. 5). Unlike the other type of array, which is made up of separate trackers 18, these arrays 50 are made up of three sensing devices 52 each comprising a respective accelerometer 54, a respective gyroscope 56 and a respective magnetometer 58. Sensing devices 52 are built into, but spread out along, the instrument 34. Instrument 34 carries one microprocessor 60, a single transmitter 62, and a common power supply or battery 64 that provides energy to the various active components. Microprocessor 60 receives data input from the accelerometer 54, the gyroscope 56 and the magnetometer 58 of each sensing device 52. The relative pose of each sensor on the respective instrument 34 is determined by the instrument's design and manufacturing process; this is the constraint that is applied to the incoming data of these arrays 50. These physical constraints provide the basis for the elimination of drift and the accurate use of dead reckoning pose acquisition, as discussed in detail previously and hereinafter. An internal reference array 50 is present in every surgical instrument 34 in the kit 40. The use of a uniform magnetic field, measured or detected through the use of a calibration sensor as described herein, provides an external reference which originates position data used either (1) as a cross-check with computer calculations based on signals from the IRAs 50 of the various instruments 34 or as a basis for registration of the instrument and patient positions.

A surgical navigation accessory system, particularly a neuro-navigation accessory system, preferably includes three separate units or types of components configured to cooperate with existing neural navigational software. The three components are (a) CT or MRI opaque fiducials 12 or a patient registration device such as a head clamp, (b) pose trackers 18, and (c) modified surgical instruments 34.

Where CT or MRI opaque fiducial(s) 12 are used, they serve to define fixed reference points by which an image of a patient's internal and external anatomy generated by CT/MRI scans can be correlated with instrument location(s) and orientation(s). The fiducials 12 can be used in determining the topography of the face FC of a patient PT (FIG. 2). Preferably, however, the patient's anatomy and cranial topography are monitored and brought into image registration via trackers 18 seated in recesses or cavities in a head clamp temporarily fixed to the patient's skull and locked into the a single fiducial or plurality of fiducials adhered to the patient's head. Thus topographical registration of the face need not be directly achieved. Topographical registration is completed automatically by the physical constraints of the array.

Figure 1:
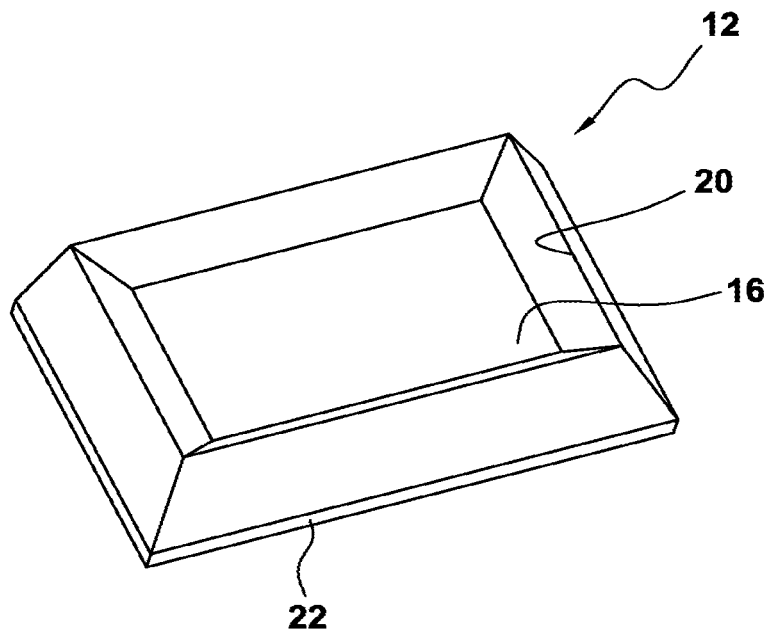
FIG. 1 is a schematic isometric view of a fiducial or marker in accordance with the present invention, for use in a surgical navigation system in accordance with the invention.

As shown in FIG. 1, fiducials 12 are preferably each in the shape of a trapezoidal prism with a depression or recess 14 on the upper side. Deposited on a base or floor of the depression 14 is a thin layer 16 of material which can be detected via CT or MRI radiation. The recess 14, above scanner-opaque layer 16, is a space in which a pose tracker 18 is seated and attached via a clip (not shown) or in a snap-lock fit with an upper edge or rim 20 of the recess. A bottom face of the fiducial 12 is coated with an adhesive layer 22.

FIG. 2 depicts an array of fiducials 12 adhered to the face FC of the patient PT in such a way as to provide topographical reference points. Preferably, fiducials 12 are attached to the head of the patient at leocations other than the face (see FIGS. 17-25 and associated description).

Figure 3:
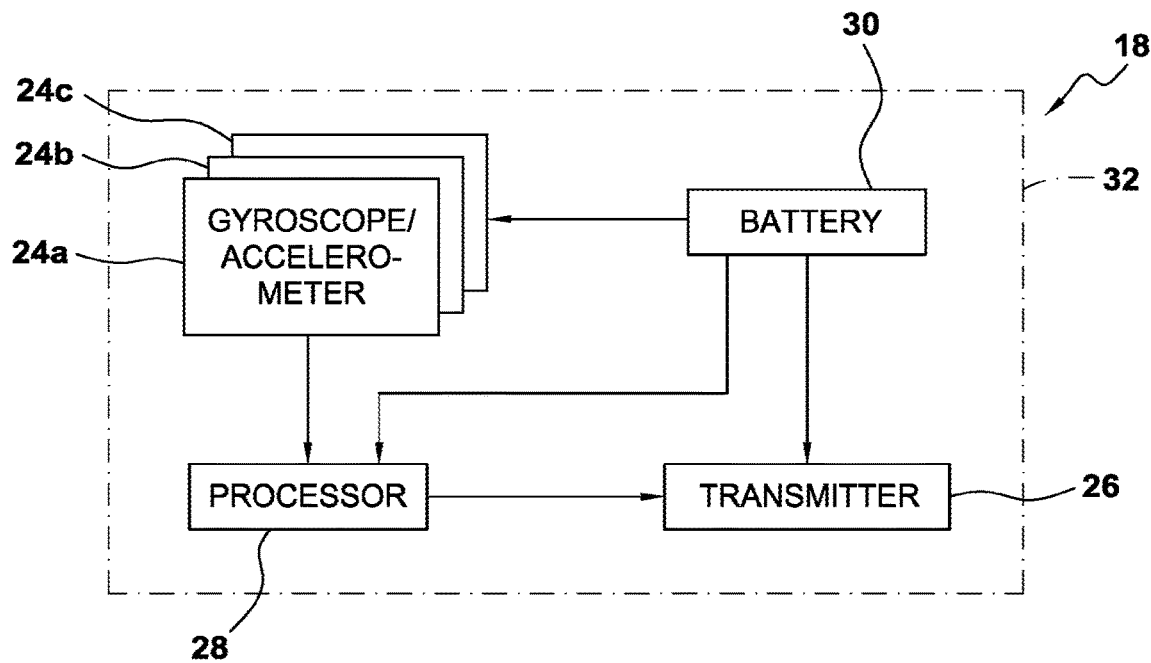
FIG. 3 is a block diagram of a position tracking unit in accordance with the present invention, for mounting to a patient via a fiducial or marker as shown in FIGS. 1 and 2, or mounting to a head clamp via recess or cavity as shown in FIG. 24, for use in a surgical navigation system in accordance with the invention.

As illustrated in FIG. 3 and as described above, each pose tracker 18 comprises four devices, namely, gyroscope/accelerometer/magnetometer assembly 24a, 24b, 24c, transmitter 26, processor or microprocessor 28, and power source or battery 30. Gyroscope/accelerometer assembly 24 generates signals in response to motion, thereby enabling a surgical navigation computer 140 (FIG. 16) to track changes in relative position and orientation (pose). Transmitter 26 is a short range wireless transmitter broadcasting data collected by the gyroscope/accelerometer assembly 24 to a receiver (not shown) in navigation computer 140. Each tracker 18 in use broadcasts at a unique frequency, or otherwise includes an identification code in its broadcast signal, thereby enabling the navigation computer 140 to distinguish the signals from different trackers. Processor 28 coordinates subunit interactions.

The subunits 24, 26, 28, 30 of each pose tracker 18 are wired together and housed in a plastic case 32 which is receivable in the recess 14 of a respective fiducial 12.

Figure 16:
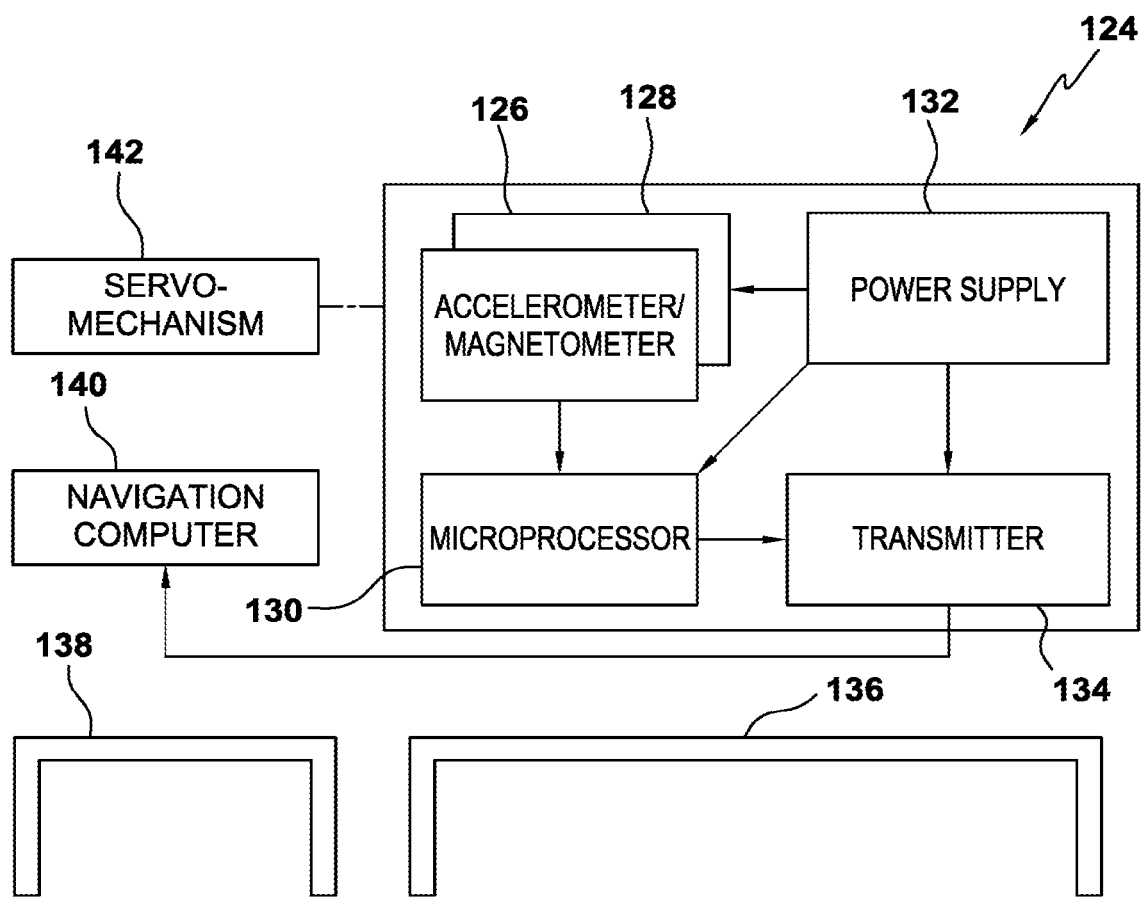
FIG. 16 is basically a block diagram showing components of a magnetic calibration apparatus in accordance with the present invention, for use in generating an external reference frame of particular use for navigational instrument tracking.

The subunits 24, 26, 28, 30 of each pose tracker 18 cooperate to transmit real-time positioning data to navigation computer 140 (FIG. 16).

Modified surgical instruments 34 are exemplarily standard neurosurgical instruments with operative tips or end effectors 35 and with pose or motion sensing devices or instrument-position trackers 52, a microprocessor 60, a transmitter 62, and a battery 64 embedded at fixed positions and orientations within handles 38 of the instruments. The sensing devices 52 together with microprocessor 60 and transmitter 62 work the same way as trackers 18, except that the system navigation software, cooperating with the on-board processors 60, creates a virtual model of each instrument 34 and overlays it into the CT/MRI image of the patient, as is consistent with existing surgical navigation technology. As discussed hereinafter, the computer software provides for elimination of external tracking and an external reference, compensating for computation drift with the provision of multiple sensing devices 52 within each instrument 34.

Each pose tracker 18 is clipped onto a fiducial 12. Trackers 18, as well as microprocessors 60 via transmitters 62, transmit real-time positioning data to a receiver connected to computer 140 of a surgical navigation system. The data from all trackers 18 and all microprocessors 60 are interpreted and coordinated with existing navigation software to provide real-time image registration.

The accessory system disclosed herein is preferably presented as a ready-to-use kit 40 schematically represented in FIG. 5. Kits 40 are surgery specific. Each kit 40 contains the necessary number of fiducials 12 and trackers 18, in addition to a specific combination of modified surgical tools 34 tailored to the procedure being done.

The layout of the components in each kit 40 is also used for calibration. Trackers 18 and instruments 34 occupy predetermined positions and orientations within a kit casing 42. The relative initial positions of every tracker 18 and instrument 34 are preprogrammed into the software and matched exactly to the place holders in the kit. (FIG. 5)

If recalibration is required at any point during the operation, the trackers 18 can be unclipped from the patient PT and returned to their starting positions within the kit 40; as are the instruments 34. Fiducials 12 remain adhered to the patient PT. Alternatively, a continual monitoring of calibration is effectuated through monitoring the positions of the trackers 18 relative to a pre-measured external magnetic field (preferably a uniform or constant magnetic field).

In a surgical procedure as contemplated, fiducials 12 are adhered to the head of the patient PT. The patient PT receives a CT/MRI scan and the surgical navigation software produces a 3D model of the patient's surgery-pertinent internal and external organic structures. The type of neurosurgical kit 40 is selected from a set of kits. The types of instruments 34 and the initial positions of trackers 18 and sensing devices 52 are preloaded into the navigation software. Trackers 18 and instruments 34 within the selected kit 40 are activated and synced with the navigation system computer 140 (FIG. 16). Each tracker 18 is clipped onto its corresponding fiducial 12. The position vector of each tracker 18 is calculated. Since their final position is a known vector from their corresponding fiducial 12, the CT/MRI image is synced with the trackers 18, and registration is complete. Surgery is performed using the modified instruments 34. Due to the sensing devices 52 and the associated microprocessors 60, the positions of the instruments 34 position within the patient, e.g., within the cranium, are known. If a new image is required intraoperatively, the trackers 18 are unclipped from the fiducials 12 and returned to their starting positions within the casing 42 of the selected kit 40. The fiducials 12 remain in position on the patient PT. Once the image is obtained, the trackers 18 can be resynced with the computer 140, and reattached to the patient PT. After completion of the procedure the kit 40, trackers 18, fiducials 12, and tools 34 can be discarded.

Figure 24:
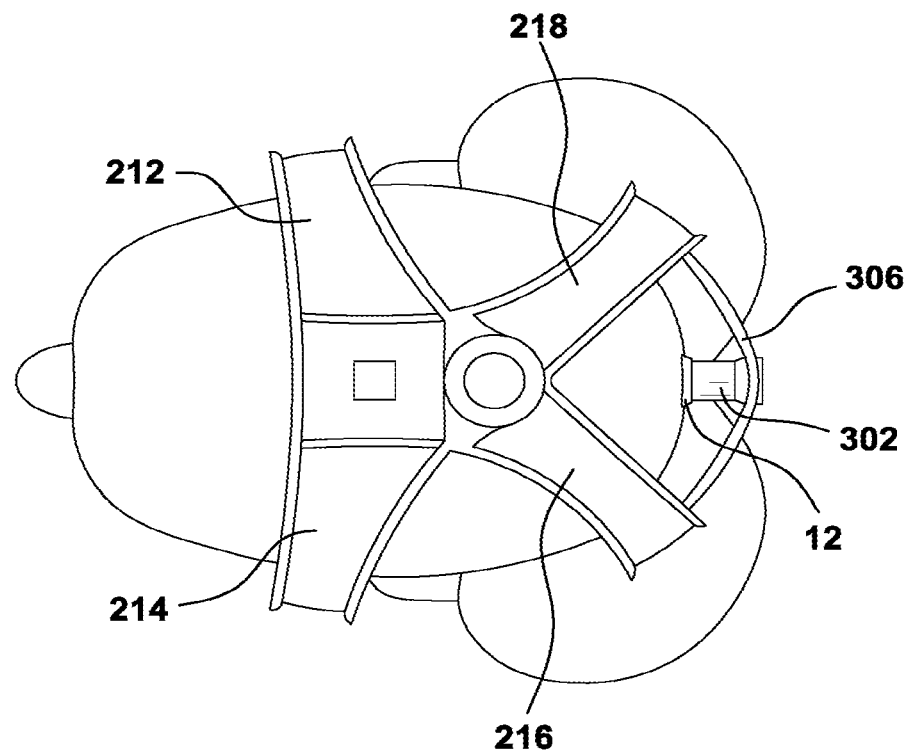
FIG. 24 is a top plan view of the cranial fixation device of FIGS. 17 and 18, showing a fiducial registered with the cranial fixation device via a connection column and a rear strut, in accordance with the invention.
Figure 25:
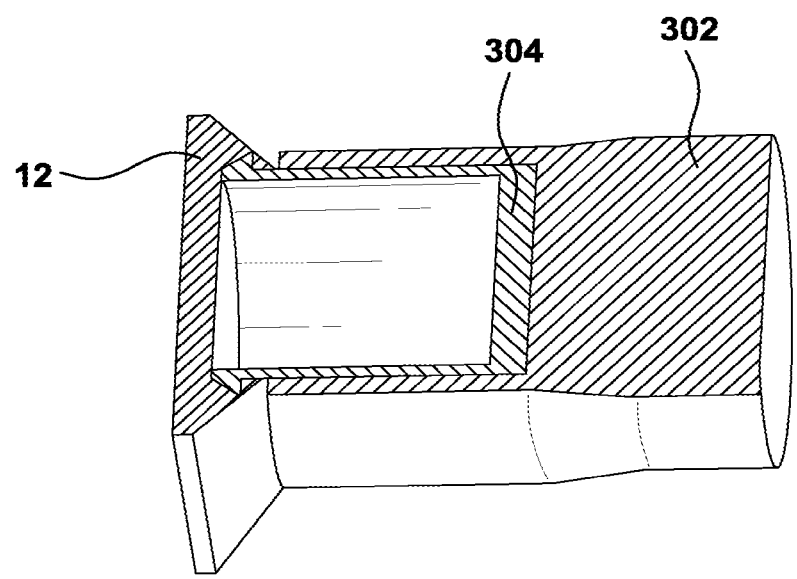
FIG. 25 is a cross-sectional perspective view of the fiducial and connection column of FIG. 24, coupled via a clip.

Using an alternative head clamp design described hereinafter in a surgical procedure, a single fiducial 12 is adhered to the head of the patient PT in a region suitable for contact with the connection column 302 (FIGS. 24 & 25). The patient PT receives a CT/MRI scan and the surgical navigation software produces a 3D model of the patient's surgery-pertinent anatomy. The type of neurosurgical kit 40 is selected from a set of kits. The types of instruments 34 and the initial positions of trackers 18 and sensing devices 52 are preloaded into the navigation software. Trackers 18 and instruments 34 within the selected kit 40 are activated and synced with the navigation system computer 140 (FIG. 16). Each tracker 18 is clipped onto its corresponding recession or cavity 212 located on the exterior of the alternate head clamp design (FIG. 24). The position vector of each tracker 18 is calculated. Since their final position is a known vector from the corresponding fiducial 12, the CT/MRI image is synced with the trackers 18, and registration is complete. Surgery is performed using the modified instruments 34. Due to the sensing devices 52 and the associated microprocessors 60, the positions of the instruments 34 position within the patient, e.g., within the cranium, are known. If a new image is required intraoperatively, the trackers 18 are unclipped from the fiducials 12 and returned to their starting positions within the casing 42 of the selected kit 40. The fiducials 12 remain in position on the patient PT. Once the image is obtained, the trackers 18 can be resynced with the computer 140, and reattached to the patient PT. After completion of the procedure the kit 40, trackers 18, fiducials 12, and tools 34 can be discarded.

The various components described herein can be implemented by existing off-the-shelf products. Pose trackers 18 can be realized by the iNEMO inertial module: 3D accelerometer, 3D gyroscope, 3D magnetometer. Processors 28 and 60 may take the form of the Arduino Pro Mini, a microcontroller board based on the ATmega328 sold by Sparkfun Electronics. Transmitters 26 and 62 may be embodied by Adafruit Bluefruit LE nRF8001 Breakout. Information about these devices and purchasing options may be found online. The general working of the sensors are described herein.

Figure 6:
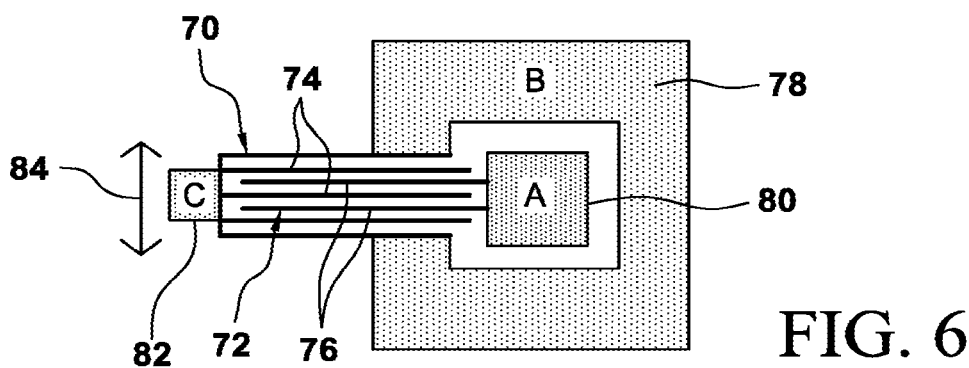
FIG. 6 is a diagram of a MEMS-accelerometer that may be used in a tracking unit (FIG. 3) or a sensing device (FIG. 4) in accordance with the present invention.

As depicted in FIG. 6, a MEMS-accelerometer for use in a tracking unit 18 or a sensing device 52 comprises two sets 70 and 72 of parallel bars or plates 74 and 76, each set 70 and 72 being electrically or operatively connected to a respective electrode 78 and 80. A mass 82 is connected to bar set 70. When a force 84 acts on mass 82, the distance between the bars 74 on the one hand and 76 on the other hand change, resulting in a measurable change in capacitance between terminals or electrodes 78 and 80. From this capacitance change, measured in volts, the acceleration of the system can be determined.

Figure 7:
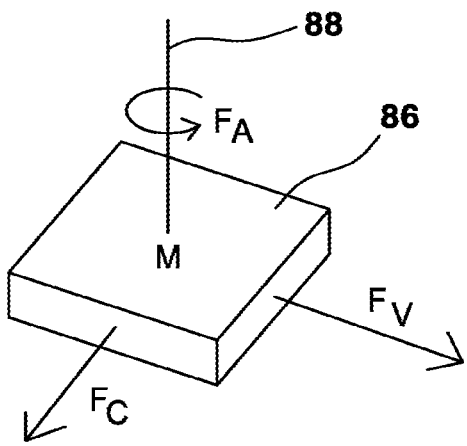
FIG. 7 is a diagram showing the Coriolis Effect.

As shown in FIG. 7, the Coriolis Effect occurs when a mass 86 moves in a rotating system, represented by rotational vector $F_A$, causing the mass to experience an additional force, the Coriolis force $F_C$, orthogonal to both the movement vector $F_V$ and axis of rotation 88.

Figure 8:
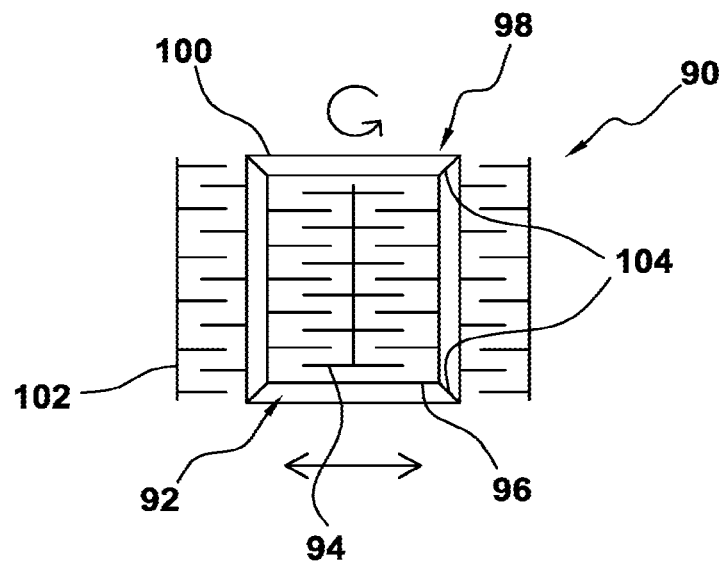
FIG. 8 is a schematic representation of a MEMS-gyroscopic sensor that may be used in a tracking unit (FIG. 3) or a sensing device (FIG. 4) in accordance with the present invention.

As illustrated in FIG. 8, a MEMS-gyroscopic rotational-motion sensor 90 comprises a capacitor 92 with electrodes 94 and 96 set on or within an oscillating structure 98 including two components 100 and 102 that rotate or oscillate relative to one another. When the system is rotated, a flexible portion 104 containing the capacitor 92 within the oscillating system experiences the Coriolis force, and alters the capacitance. This measurable signal is translated into a change in one of the Euler angles in terms of angular velocity.

Figure 9:
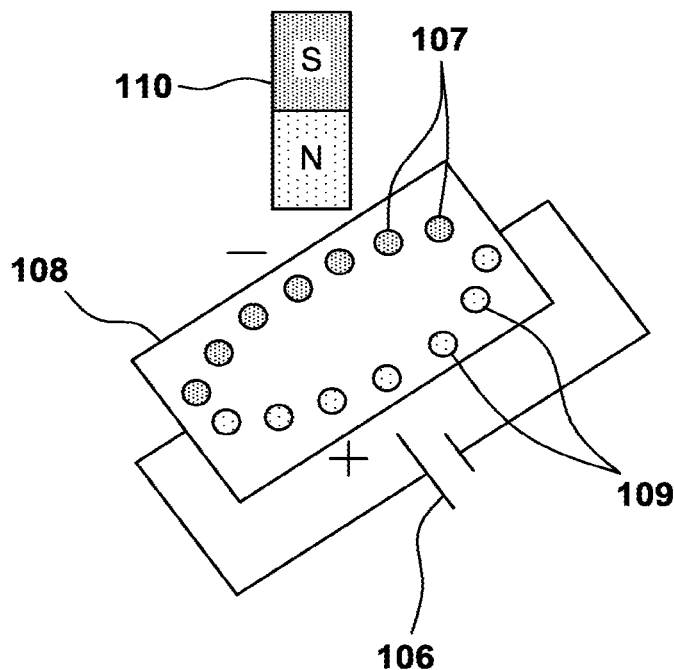
FIG. 9 is a diagram depicted a MEMS-magnetometer 1DOF, which is based on the Hall Effect, utilizable in a tracking unit (FIG. 3) or a sensing device (FIG. 4) in accordance with the present invention.

FIG. 9 depicts operative components of a a MEMS-magnetometer 1-DOF. When a current from a current source 106 passes through a conductive plate 108, the current follows the path of least energy, which, when there is no interference, is a straight line. Pursuant to the Hall Effect, the presence of a magnetic field, represented by a magnet symbol 110, will deflect the path of the current, causing one side of the plate 108 to be negatively charged (107) and the other to be positively charged (109). By measuring the charge differential, the strength of a magnetic field passing through that plane can be calculated. The strongest magnetic field is magnetic north.

In each instrument 34, the physical constraints of sensing devices 52, or in other words, the fixed positions and fixed orientations relative to one another, provide the basis for the elimination of drift and the accurate use of dead reckoning pose acquisition. Consider the matrix A:

$$A = \begin{bmatrix} i_A & j_A & k_A \\ \theta_A & \varphi_A & \rho_A \end{bmatrix}$$

Where i, j, & k are values of position on a Cartesian axis, and theta, phi & rho are values of yaw, pitch, and roll, or Euler angles. These six degrees of freedom represent pose, as calculated from the 9-DOF collected by the IMU in the forms of acceleration, angular rate, and magnetic field strength, each in three dimensions.

Matrix A represents the pose on only one tracker. The pose of each tracker can be defined by a matrix, A through n; where n is the total number of Pose Trackers in use.

$$B = \begin{bmatrix} i_B & j_B & k_B \\ \theta_B & \varphi_B & \rho_B \end{bmatrix} \dots n = \begin{bmatrix} i_n & j_n & k_n \\ \theta_n & \varphi_n & \rho_n \end{bmatrix}$$

Figure 10:
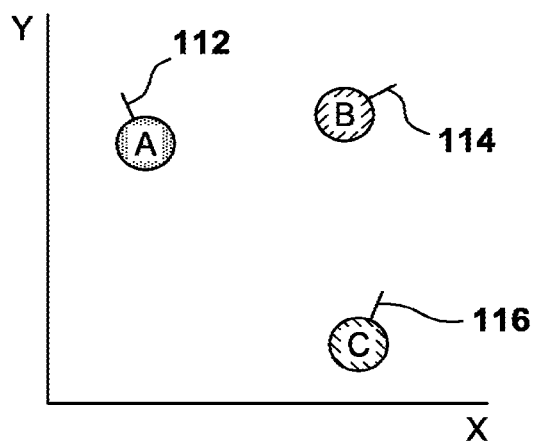
Figure 11:
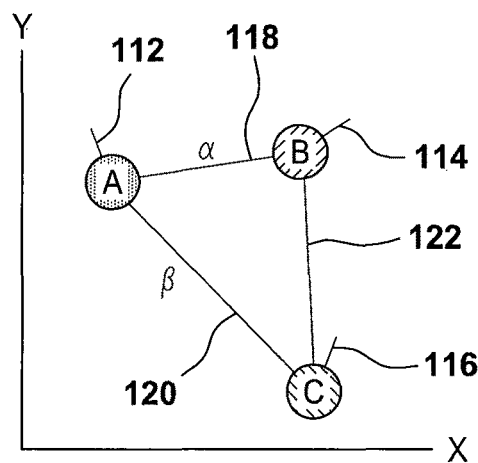

This set of matrices, however, has no frame of reference and is, thus, undefined (FIG. 10). As mentioned, the relative positions of each tracker is defined. Therefore, there exists a known matrix representing the translation and rotation of the each Pose Tracker relative to another (FIG. 11).

$$\alpha = \begin{bmatrix} i_\alpha & j_\alpha & k_\alpha \\ \theta_\alpha & \varphi_\alpha & \rho_\alpha \end{bmatrix} \dots \omega = \begin{bmatrix} i_\omega & j_\omega & k_\omega \\ \theta_\omega & \varphi_\omega & \rho_\omega \end{bmatrix}$$

Designating one matrix, say matrix A, as the primary point of reference within the system, the positions of the other Pose Trackers can be defined $$B = \alpha + A \dots n = \omega + A$$

Figure 12:
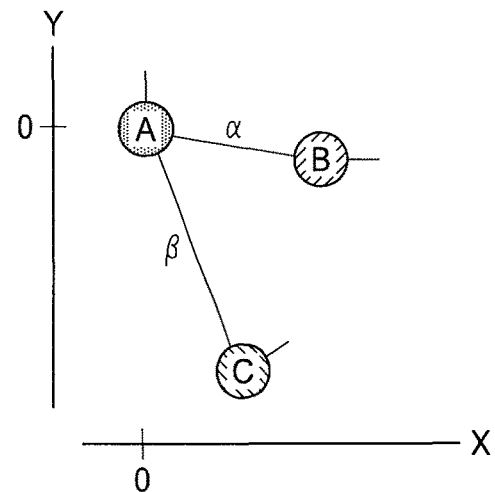

We now have a complete set of defined matrices. We will call this set R (FIG. 12).

$$R = \begin{Bmatrix} A \\ B \\ \vdots \\ n \end{Bmatrix}$$

R is determined by the use of fiducials and CT imaging, predetermined recesses or cavities found on the head clamp, or predetermined designs of the modified surgical instruments. This internal reference array represents a physical constraint on the system.

Provided that a system has multiple IMUs which are separated by known distances and fixed orientations relative to each other, if there is a change in pose of any Pose Tracker that violates the defined constraints of R, it can be determined that the calculated change in pose does not represent accurate physical movement of the tracker; rather it could be a product of noise or drift. For example, consider a system comprised of three Pose Trackers, A, B & C. If it known that $$\begin{Bmatrix} A \\ B \\ C \end{Bmatrix} \equiv \begin{Bmatrix} A \\ A+\alpha \\ A+\beta \end{Bmatrix} = R$$

Say the data from Pose Tracker B is calculated and shows a positive vertical translation of some value, z, over the interval $t_0$ to $t_1$.

$$\Delta B|_{t_0}^{t_1} = \begin{bmatrix} 0 & 0 & z \\ 0 & 0 & 0 \end{bmatrix}$$

However, the data from Pose Trackers A and C is calculated and suggests no positive vertical translation.

$$\Delta A|_{t_0}^{t_1} = \Delta C|_{t_0}^{t_1} = \begin{bmatrix} 0 & 0 & 0 \\ 0 & 0 & 0 \end{bmatrix}$$

The incongruence of the resulting data violates the constraint.

$$\begin{Bmatrix} A+\Delta A \\ B+\Delta B \\ C+\Delta C \end{Bmatrix} \neq \begin{Bmatrix} A \\ A+\alpha \\ A+\beta \end{Bmatrix} \equiv R$$

Figure 13:
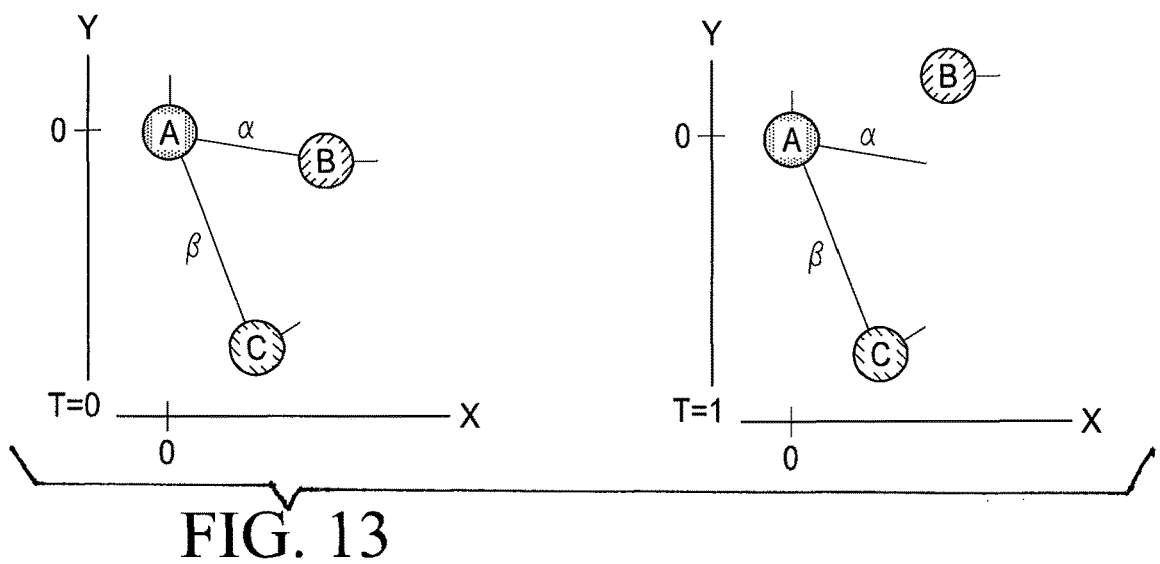

In this example, because Pose Trackers A and C agree exactly, we can suggest that the change in pose as calculated from the data of Pose Tracker B can be ignored (FIG. 13). If, however:

$$\Delta A|_{t_0}^{t_1} = \Delta B|_{t_0}^{t_1} = \Delta C|_{t_0}^{t_1} = \begin{bmatrix} x & y & z \\ 0 & 0 & 0 \end{bmatrix}$$

Or there exists some set of $\Delta A$, $\Delta B$, & $\Delta C$ in which:

$$\begin{Bmatrix} A+\Delta A \\ B+\Delta B \\ C+\Delta C \end{Bmatrix} = \begin{Bmatrix} A \\ A+\alpha \\ A+\beta \end{Bmatrix} \equiv R$$

Then, the calculated movement, in this example translation without rotation, is valid and represents true physical movement (FIG. 14).

The above examples are simplistic, and do not necessarily convey the complicated nature of real world application. Particularly, when noise, drift, and true movement are incorporated into the signal. To overcome this, the number of Pose Trackers can be increased. A larger population increases the probability that the true movement will be identifiable from within the signals.

Furthermore, redundancy within the definition of R, i.e. defining multiple points of reference, may help with accuracy.

$$\begin{Bmatrix} A \\ A+\alpha \\ A+\beta \end{Bmatrix} \equiv R \equiv \begin{Bmatrix} \beta \\ \beta+\gamma \\ \beta+\delta \end{Bmatrix}$$

Once again, the above examples are simplistic. In practice, Set R will almost never be maintained between intervals. To remedy this the data must be manipulated.

Consider the pose of trackers A, B & C at some time, t. The calculated movement of each tracker between time t and time t+1 is designated by delta, $\Delta$. The sum of each pose and change in pose is, ideally, equal to Set R as defined in the constraint.

$$\begin{Bmatrix} A_t+\Delta A \\ B_t+\Delta B \\ C_t+\Delta C \end{Bmatrix} = \begin{Bmatrix} A \\ A+\alpha \\ A+\beta \end{Bmatrix}$$

This will rarely be the case. Rather, each tracker will be defined by its own unique pose. Since Tracker A is our primary reference, we can use the constraint to redefine each possible pose as $A_1$, $A_2$, & $A_3$.

$$\begin{Bmatrix} A_t+\Delta A \\ B_t+\Delta B-\alpha \\ C_t+\Delta C-\beta \end{Bmatrix} = \begin{Bmatrix} A_1 \\ A_2 \\ A_3 \end{Bmatrix}$$

$A_1$, $A_2$, & $A_3$ each have their own associated Gaussian probability density that are determined by the properties of both the system and the sensors. In most instances the densities will overlap. In the unlikely case one density differs significantly from the others, it can be removed as an outlier. The probability densities can be multiplied and the most probable pose can be determined and defined as $A_{true}$ (FIG. 15).

Using the constraint, the pose of each tracker, and thus the array as a whole, can be calculated at time, t+1.

$$\begin{Bmatrix} A_{t+1} \\ B_{t+1} \\ C_{t+1} \end{Bmatrix} \equiv \begin{Bmatrix} A_{true} \\ A_{true}+\alpha \\ A_{true}+\beta \end{Bmatrix} = R$$

This process is repeated for all intervals of time.

FIG. 10 shows three trackers A, B, and C without a reference frame. Trackers, A, B, and C are located somewhere in space. The exact location to the origin (represented by the XY-axes) cannot be determined. Their headings are represented by the lines 112, 114, 116 pointing from each tracker A, B, C, can technically be determined due to the constant and uniform forces of gravity and magnetic north. However, their initial conditions must be verified by the CT imaging or manufacturing standards.

FIG. 11 shows three trackers A, B, C with predetermined physical constraints 118, 120, 122. Based on these known physical constraints of the system derived from either the CT imaging or the design of the respective surgical instrument (34), the distances and orientations of each tracker, A, B, & C are known. The distance vectors 118 and 120 are alternately defined here as alpha and beta.

FIG. 12 illustrates the solution of identifying one tracker, say A, a primary reference. Its position is designated as the origin, while the position of trackers B and C are defined by vectors alpha and beta, respectively. The orientation of tracker A is designated as zero as well. The orientation of the trackers is adjusted accordingly. Together, the true relative poses of the three trackers is defined as Set R.

FIG. 13 depicts the situation when there is erroneous movement on the part of one tracker, deemed an outlier. The incoming data is used to calculate change in pose over some interval of time and it is determined that the relative positions and orientations of trackers A and B violate the constraint 118, 120, and/or 122. The relative poses of trackers A and C, however, indicate that there was no movement. Based on the agreement of trackers A and C, the movement calculated from tracker B's data can be considered erroneous.

FIG. 14 depicts ideal movement. The incoming data is calculated and the results do not violate the known constraint. Therefore, the suggested movement of each tracker, in this case translation without rotation, is considered true, and the initial position of each tracker is updated and ready for the next calculation.

FIG. 15 depicts statistical treatment of incongruent results. More-often-than-not, the calculated movements of both trackers will violate the constraint. None of the trackers can be considered as the correct frame of reference. Since tracker A is our primary reference, we can use the constraint and the proposed movements calculated from each tracker to redefine each possible pose of the array as a whole. From here we can see three possible poses of A, clustered together, but with slightly varying positions and orientations. The most probable pose is determined statistically and is defined as the true pose of tracker A. The true poses of trackers B and C are then calculated as not to violate physical law. The updated position can then be used for calculations over the next interval of time.

As depicted in FIG. 16, magnetic calibration apparatus 124 for sensing a magnetic field and determining magnetic field vectors throughout a predetermined spatial region, exemplarily in a surgical operating room, includes a 3-DOF calibration magnetometer 126 and 3-DOF calibration accelerometer 128, a microcontroller 130, a power supply 132 and a wired or wireless transmitter 134. The calibration magnetometer 126 may be incorporated into the kit 40 or provided separately. The calibration apparatus 126 must be located on a level surface 136 adjacent an operating table 138. All sensors disclosed herein, particularly including calibration magnetometer 126 and 3-DOF calibration accelerometer transmit data to navigation computer 140. More particularly, data from the calibration magnetometer 126 and 3-DOF calibration accelerometer are transmitted to a navigation computer 140 via microcontroller 130 and transmitter 134.

Calibration apparatus 124 is required for implementing an external reference navigation method as described herein. Within this apparatus, calibration sensors 126 and 128 are moved automatically and in a controlled fashion by a servo-mechanism 142 (exemplarily including encoders and electric motors) along a predetermined path in a region about operating room table 138. The path may be determined by tracks built into the kit 40, for example. Data is collected and transmitted to computer 140 that is used to identify and map the volume in which the trackers 18 operate. The process may be termed "mobile calibration."

The initial positions and types of instruments 34 are preloaded in encoded form into the navigation computer 140 for informing the navigation software. This magnetic navigation system is used in tandem with the statistical methods or error reduction implemented via data from Internal Reference Arrays, exemplarily arrays 50 in surgical instruments 34, discussed above.

A two-stage calibration is required for magnetic navigation: static calibration and mobile calibration. The goal of static calibration is to confirm that the local magnetic field, in the operating room, is static. The calibration accelerometer 126 is provided to confirm that the calibration apparatus 124 is indeed level.

Once level, the calibration magnetometer 128 is used while it is stationary. This allows the user to determine the general direction of the strongest magnetic field. If the vectors fluctuate significantly while stationary, the local magnetic field is considered to be dynamic and magnetic navigation will not be applicable. Assuming the field is static, the user can determine the position of the source of the strongest magnetic field. Depending on the strength of secondary sources, this may or may not be magnetic north. As-long-as this source is stationary, the identity of the source is irrelevant.

Once static calibration is complete and the requirements for magnetic navigation are met, mobile calibration can proceed. The goal of mobile calibration is to collect enough data to determine a 3D vector field map describing the magnetic vector as a function of position. In this step, the calibration sensor 128 is moved by servo-mechanism 142 preferably under the control of navigation computer 140 along a particular path within the field of operation at a controlled rate such that the acceleration and position of the sensor 129 are known as a function of time. Servo-mechanism 142 may exemplarily include a robotic arm (not shown) with a distal end holding the calibration sensor 128 for movement along a predetermined path in space about surgical operating table 138; this is achieved by the calibration apparatus 124. Servomechanism 142 includes encoders or other position tracking sensors so that the 3D position of calibration sensor 128 is known at-all-times during a calibration or field measurement process. Position is of more concern than orientation during mobile calibration. Therefore, the orientation of the calibration sensor 128 can remained fixed. The calibration sensor 128 must move in or along all three axes in a Cartesian coordinate system.

The data from the mobile calibration is constructed by navigation computer 140 into a three-dimensional vector field mapping magnetic vectors as a function of position. The resultant vector field will be most accurate within the volume that was measured by the calibration sensor 128. However, the field of operation exceeds the volume measured, therefore the vector field must be extrapolated. Consequently, the level of accuracy of a point within the vector field is inversely proportional to its distance relative to the arbitrary origin defined by the calibration sensor 128. As a result, the kit or calibration apparatus 124, should be positioned near the patient's location on table 138 within the operating room.

The calibration apparatus 124 remains stationary once mobile calibration is completed. If fluctuations in the magnetic field are identified by the calibration magnetometer 128 and/or movement is detected by the calibration accelerometer, the system will notify the user via the user interface of the navigation computer 140 and the system can be recalibrated.

The navigation apparatus and methodology described hereinabove may be utilized in a neurosurgical procedure with a neurosurgical head clamp or fixation device that is approach specific. The approaches include bifrontal coronal craniotomy (FIGS. 17 and 18), pteryonal craniotomy (FIG. 21), and retrosigmoid craniotomy (FIG. 23). A combined pteryonal retrosigmoid approach specific clamp (FIG. 22) is also contemplated. Each head clamp is pre-formed with a set space available for craniotomy exposure.

FIGS. 17 and 18 depict a head clamp or cranial fixation device 210 configured for a bifrontal neurosurgical approach and allows extension to a full coronal craniotomy. Head clamp 210 is a rigid frame that comprises four arms 212, 214, 216, and 218 that connect to one another in a hub 220 locatable at a superior apex of the patient's head PH. Arms 212, 214, 216, 218 are arcuate members that extend down the sides of the patient's head PH at various angles. Two anterior arms 212 and 214 extend laterally opposite one another and, when the device is in operative position, are positioned anterior to the patient's ears PE1, PE2. Two posterior arms 216 and 218 extend down the back of the head PH at approximately forty five degrees equidistant from a midsagittal plane P1. The positioning of the arms 212, 214, 216, 218 leaves much of the anterior portion of the head and the forehead unobstructed for a frontal, bifrontal, or full coronal craniotomy.

The arms 212, 214, 216, 218 are curved as to fit around the superior half of the head. Headframe 210 is not designed to fit snuggly around the head; rather there should be space between the patient and the head clamp. Due to the variety of shapes of the human skull and varying amounts of tissue, some contact may occur. The interior aspect of the head clamp 10 including each of the arms 212, 214, 216, 218 is coated with rubber or some similar polymer. As the primary structure of the headframe 210 is composed of a hard and sturdy plastic, this layer of rubber on the interior will prevent undesired force/pressure on the patient. In addition, this layer of rubber will help to dampen any vibrational forces caused by surgical drills, reducing the likelihood of failure of the head clamp.

Typically, anterior arms 212 and 214 are disposed in a common plane P2. The arms 212, 214, 216, 218 collectively define four gaps or inter-arm spaces 222, 224, 226, 228 including three 222, 224, 226 on one side (rear or posterior side) of the common plane P2 and one 228 on an opposite side (anterior side) of the common plane.

Figure 22:
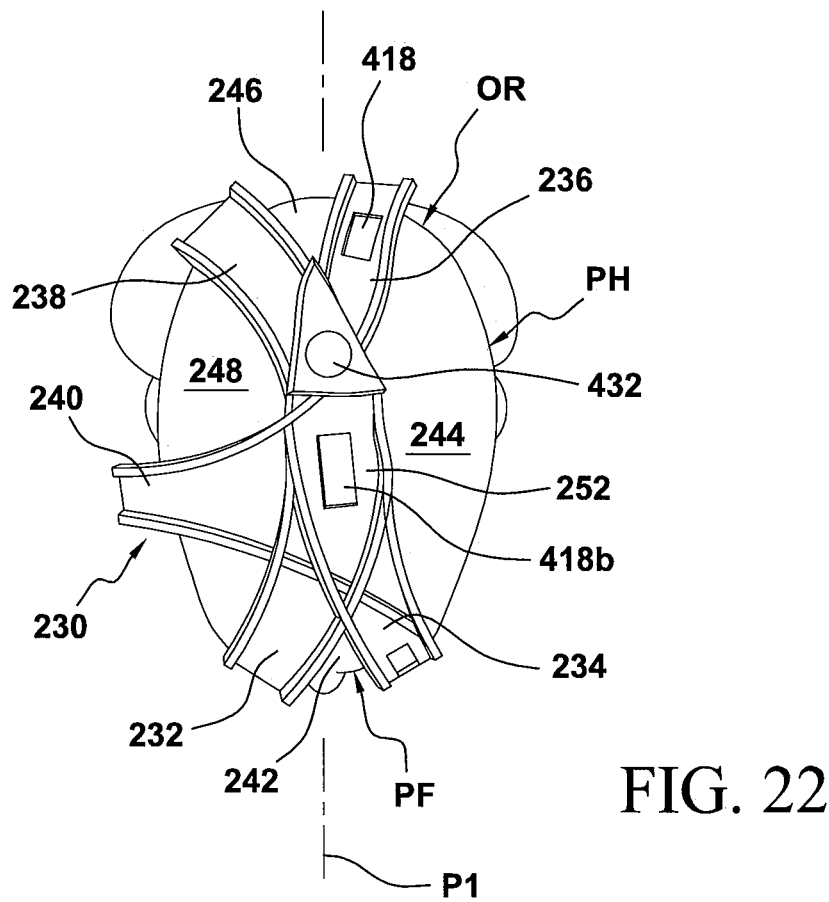
FIG. 22 is a top plan view of a modification of the cranial fixation device of FIG. 21, configured for combined pteryonal-retrosigmoid craniotomy, showing the device in position on a subject.
Figure 23:
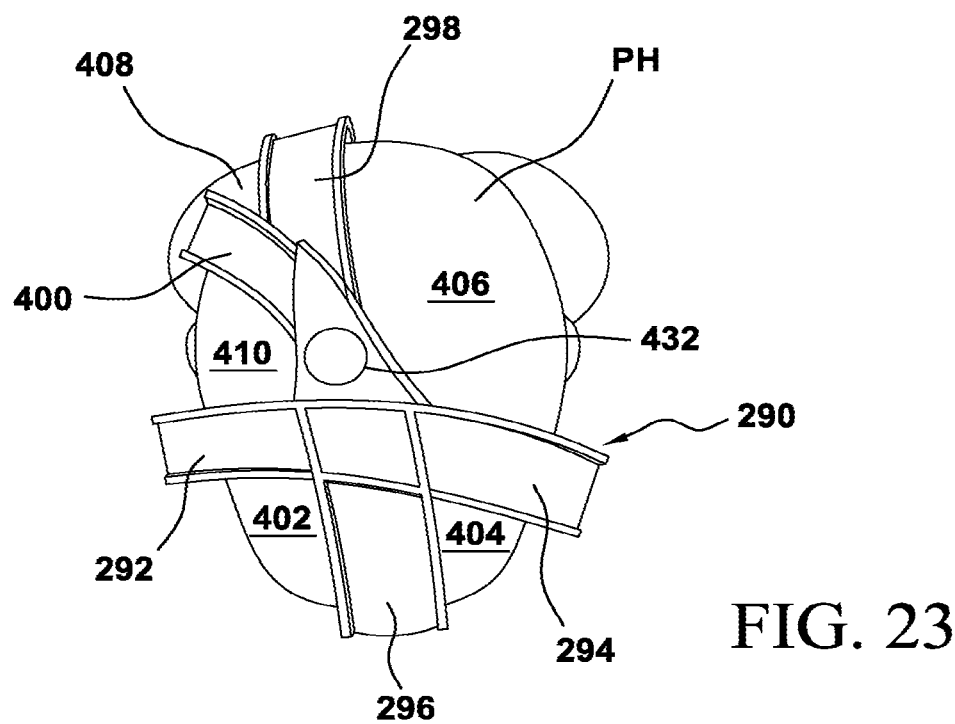
FIG. 23 is a top plan view of a third embodiment of a cranial fixation device in accordance with the present invention, configured for retrosigmoid craniotomy, showing the device in position on a subject, the fixation device being utilization in a neurosurgical operation with surgical navigation as described herein.

As illustrated in FIG. 22, a second approach-specific head clamp or cranial fixation device 230 is a rigid frame that includes two anterior arms 232 and 234 angled with respect to one another and configured to extend down over the patient's forehead PF in vertical alignment with respective eyes (not shown) of the patient. The device 230 further includes two posterior arms 236 and 238 angled with respect to one another and configured to extend down over the occipital region OR of the patient's head PH. An additional arm 240 is configured to extend laterally and anterior to an ear PE1 of the patient. This embodiment 230 is adapted for use in a pteryonal craniotomy.

Arms 232, 234, 236, 238, and 240 of head clamp or cranial fixation device 230 collectively define five gaps or inter-arm spaces 242, 244, 246, 248, and 250 between adjacent arms, which are connected to one another in a hub region 252 that is disposable generally centrally atop the patient's head PH. One of the gaps or inter-arm spaces 244 subtending an angle of greater than 90 degrees and each of the other gaps or inter-arm spaces 242, 246, 248 and 250 subtend an angle of less than ninety degrees. The largest gap or inter-arm space 244 is disposed between anterior arm 234 and posterior arm 236.

Figure 21:
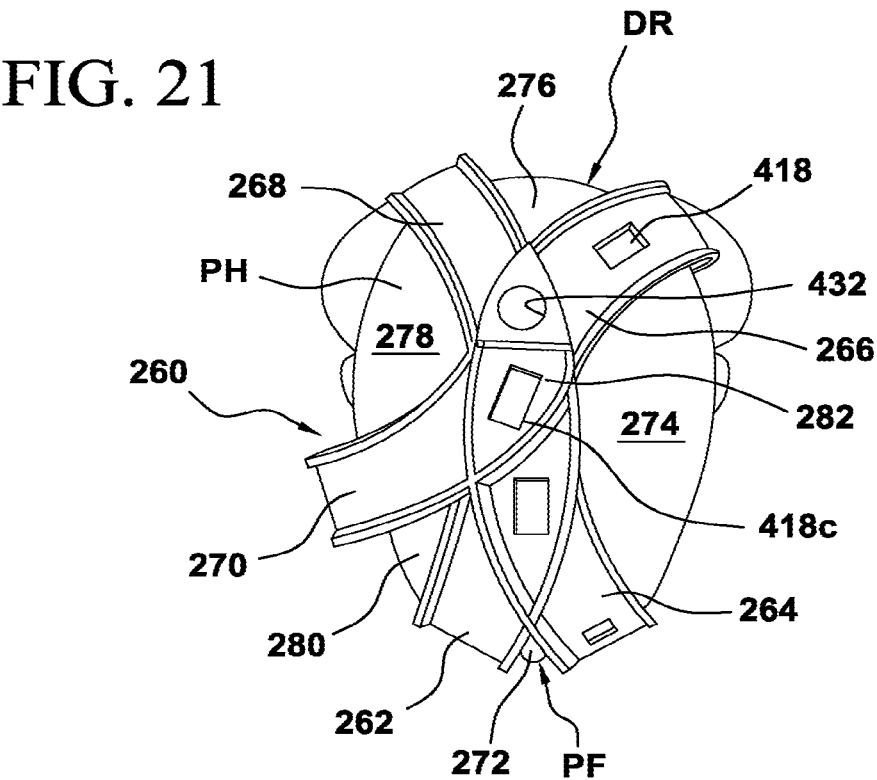
FIG. 21 is a top plan view of a second embodiment of a cranial fixation device in accordance with the present invention, configured for pteryonal craniotomy, showing the device in position on a subject, the fixation device being utilization in a neurosurgical operation with surgical navigation as described herein.

FIG. 21 shows a head clamp or cranial fixation device 260 that is similar to head clamp or device 230, but with arms that are slightly turned relative to those of head clamp 230. Accordingly, head clamp or cranial fixation device 260 is a rigid frame that includes two anterior arms 262 and 264 angled with respect to one another and configured to extend down over the patient's forehead PF in vertical alignment with respective eyes (not shown) of the patient. The device 260 further includes two posterior arms 266 and 268 angled with respect to one another and configured to extend down over the occipital region OR of the patient's head PH. An additional arm 270 is configured to extend laterally and anterior to an ear PE1 of the patient. Head clamp or cranial fixation device 260 is configured to define five gaps or inter-arm spaces 272, 274, 276, 278, 280 between adjacent arms, with two of the gaps or inter-arm spaces 274 and 278 each subtending an angle of greater than 90 degrees. Gaps or inter-arm spaces 272, 276 and 280 each subtend an angle of less than ninety degrees. Gap or inter-arm space 274 is disposed between anterior arm 264 and posterior arm 266, while gap or inter-arm space 278 is disposed between additional or lateral arm 270 and posterior arm 268. Arms 262, 264, 266, 268, and 270 converge and join to one another at a hub region 282 in a superior or apex.

As illustrated in FIG. 23, a head clamp or cranial fixation device 290 includes two anterior arms 292 and 294 each configured to extend laterally and anterior to a respective ear PE1 and PE2 of the patient. An additional anterior arm 296 is configured to extend down over the patient's forehead PF in vertical alignment with the bridge of the patient's nose (not shown). Two posterior arms 298 and 400 are angled with respect to one another and configured to extend down on one side of the patient's head posterior to one ear PE1 (of PE2 in a mirror-image version of this head clamp). This head clamp 290 is adapted for use in a retrosigmoid craniotomy.

Arms 292, 294, 296, 298 and 400 of head clamp or cranial fixation device 290 collectively define five gaps or inter-arm spaces 402, 404, 406, 408, and 400 between adjacent arms. Specifically two of the gaps or inter-arm spaces 402 and 406 may each subtend an angle of greater than 90 degrees, while each of the other three gaps or inter-arm spaces 404, 408 and 410 subtend an angle of less than ninety degrees. Gap or inter-arm space 406 is disposed between anterior arm 294 and posterior arm 298, while gap or inter-arm space 402 is disposed between additional or forehead arm 296 and anterior arm 292.

Figure 20:
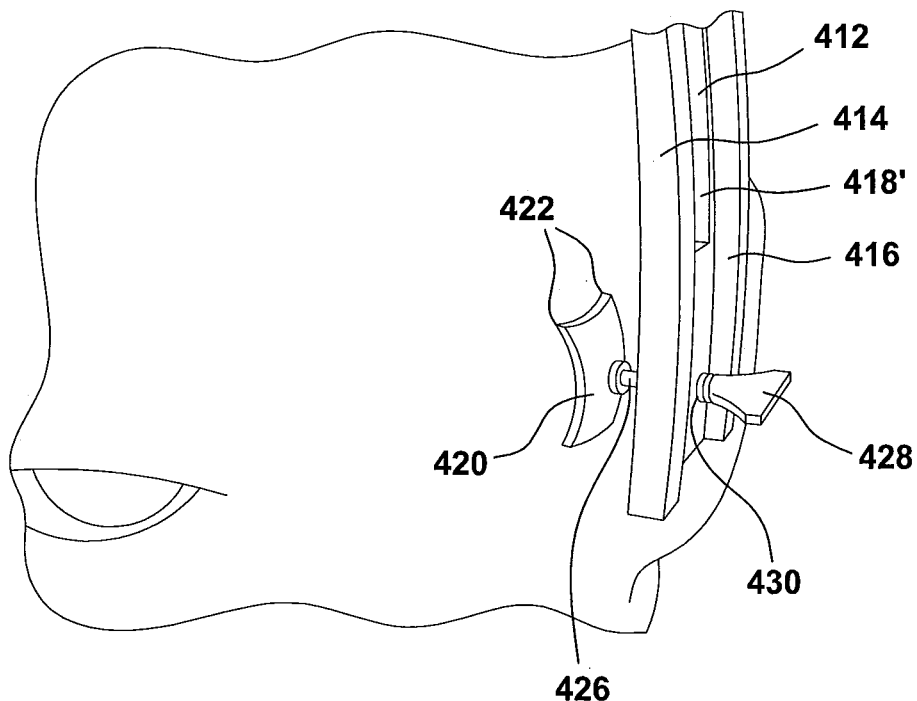
FIG. 20 is a partial front and left side perspective view, on a larger scale, of the cranial fixation device of FIGS. 17 and 18, showing the head contact member and a mounting assembly of FIG. 19 attached to an anterior arm of the cranial fixation device.

The arms of each head clamp or cranial fixation frame 210, 230, 60, 290 each include a central body portion 412 two flanges 414 and 416 extending along longitudinal edges of the central body portion perpendicularly thereto (see FIG. 20). Flanges 414 and 416 serve as stiffening ribs for increasing or enhancing the rigidity of the arms.

The arms of each head frame or cranial fixation device 210, 230, 260, 290 each have a superstructure including central body portion 412 and flanges or ribs 414 and 416 made of hard and sturdy polymeric material. As indicated above, each of the arms may be each coated on an interior or concave side (facing the patient's head PH) with a layer of resilient material.

Figure 19:
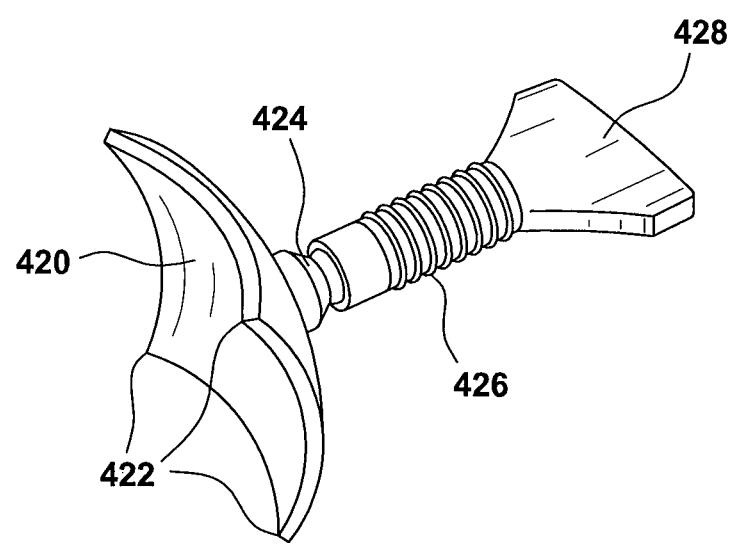
FIG. 19 is a perspective view of a head contact member and a mounting assembly included in a cranial fixation device in accordance with the present invention.

The arms of each head frame or cranial fixation device 210, 230, 260, 290 are each provided at a free end with a respective head contact member 420 (FIGS. 19 and 20). Head contact member 420 has an arcuate body and a plurality of ends or corners 422. Head contact member 420 is configured so that the ends or corners 422 are disposable in contact with the patient's head PH while the body of the contact member remains spaced from the patient's head PH.

More particularly, the arcuate body of contact member 420 is a plate in the form of a spherical section having at least three, and preferably four, ends or corners 422. Head contact member 420 is configured so that the ends or corners 422 thereof are disposable in contact with the patient's head PH while a major portion of the plate 420 remains spaced from the patient. Typically head contact member has a shape formed by a projection of a square onto a sphere such that a normal vector at a centroid of the square equals a normal vector of the sphere.

The spherical section forming the head contact member or plate 420 is a sphere that has a smaller radius of curvature than the head of the patient. For purposes of simplifying manufacture by having uniform parts, head contact members or plates 420 are all identical and have a radius of curvature smaller than any skull surface into engagement with which any contact plate 420 might be placed.

Preferably, head contact member 420 is connected, in a manor such that it can pivot, to the free end of the respective arm 212, 214, 216, 218, 232, 234, 236, 238, 240, 262, 264, 266, 268, 270, 292, 294, 296, 298, 400. As shown in FIG. 19, head contact member 420 is connected via a ball-and-socket universal joint 424 to an end of an externally threaded pin or screw 426 provided at an opposite end with a wing flange 428. This wingnut screw 426 is a coupling configured to enable a surgeon to adjust a distance between the respective head contact member 420 and the free end of the respective arm to which the contact member is mounted. The mounting of contact member 420 to an arm of a head frame or cranial fixation device 210, 230, 260, 290 has one translational degree of freedom and three rotational degrees of freedom. In this way, the four vertices of the square make contact at four separate points and distribute the force equally such that the head is secure without causing damage to the patients via piercing the skin and damaging underlying tissues, or via pressure necrosis. This system, while maintaining stabilization, is noninvasive and thus does not enter the boney skull and allow for the formation of abscesses in the postoperative period. In the event that this modified stabilizing pin is undesirable for the surgery, a traditional bone pin can be inserted.

Pin or screw 426 traverses a hole 430 (FIG. 20) at the free end of the respective head clamp arm. A washer or dampener (not shown) is placed around the hole on both the interior and exterior aspects of the headframe 210, 230, 260, 290 between contact member or plate 420 and wingnut flange 428, respectively.

Each head clamp or cranial fixation frame 210, 230, 260, 290 is provided in one or more arms with one or more generally quadrilateral or rectangular apertures or cutouts 418 in central body portion 412 of the arms for enabling access through the central body portion to the patient's head PH. The access is advantageous, for instance for the placement and attachment of fiducial markers for a navigation and imaging system.

Preferably each head clamp or cranial fixation frame 210, 230, 260, 290 is provided with at least seven quadrilateral shaped cutouts 418 extending through the body of the headframe. One 418a (FIGS. 17 and 18), 418b (FIG. 20), 418c (FIG. 21) is positioned at the superior aspect of the headframe proximate to and anterior of the apex (not labeled) of the patient's head or skull PH.

With-reference-to head clamp or cranial fixation frame 210 (FIGS. 17 and 18), two quadrilateral shaped cutouts 418' are formed in each of anterior arm 212 and 214 (totaling 4) positioned above the threaded screw hole 430 (FIG. 17) and separated by a predetermined distance. Only one cutout 418" is provided in each posterior arm 216 and 18, again above the respective threaded screw hole.

Cutouts 418, 418a, 418b, 418c, 418', 418" are provided to allow for the placement of fiducials onto the patient's head in compliance with a self referential pose tracking system for intracranial and spinal neuro-navigation as described above. Pose trackers 18, as described above, lock in to both the fiducials 12 and the headframe via a rubber or soft polymer connecting piece designed to dampen any vibrational energy caused by the surgical instruments especially drills. This setup prevents movement of the fiducials due to the movement of skin caused by sagging or changes in tension after incisions are made. This connection also helps to prevent the relative movement between the trackers, satisfying the system requirements for the internal reference array as described above.

Ribs or flanges 414, 416 extend the length of the arms 212, 214, 216, 218, 232, 234, 236, 238, 240, 262, 264, 266, 268, 270, 292, 294, 296, 298, 400 and intersect one another about the superior portions or hub regions of the head clamp or frame 210, 230, 260, 90 where the arms meet. The ribs 414, 416 are present to add strength and resist flexion and extension of the arms 212, 214, 216, 218, 232, 234, 236, 238, 240, 262, 264, 266, 268, 270, 292, 294, 296, 298, 400.

Head clamp or cranial fixation frame 210, 230, 260, 290 can be directly applied to a head frame unique to its design following application to the patient. The head clamp can be placed and positioned with the head of the bed in place and the head frame can then be applied. Thus, the head of the patient is at no point unsupported while applying the head clamp.

To that end each clamp head 210, 230, 260, 290 is provided with a socket 132 at the hub region of the respective head clamp for immobilization by connection with a head frame.

The pteryonal approach-specific head clamp allows some extension to the posterior fossa. All technical aspects of the bifrontal head clamp are present in the pteryonal head clamp. The only difference is the position of the arms and how they fit around the patient's head.

In head clamp or cranial fixation frame 230, rather than having two anterior arms 212 and 214 that extend laterally as in head clamp or cranial fixation frame 210, one anterior arm 234 extends down a portion of the forehead PF. The position of posterior arm 236, same side as the anterior arm 234, is shifted slightly towards the midsagittal plane P1. The positioning of the arms leaves much of the side of the head PH unobstructed (space 244) for a pteryonal- or combined pteryonal-retrosigmoid-approach. These head clamps are not symmetrical, therefore there are 'left' and 'right' varieties which are mirror images. The correct headframe corresponding to the preferred side of the head can be chosen and in this way is approach specific.

The unilateral retrosigmoid approach specific head clamp 290 (FIG. 23) allows extension to midline as well as some exposure of the anterior fossa through temporal- or modified-pteryonal approach.

As illustrated in FIGS. 24 and 25, a fiducial 12 attached to the head HD of a patient is registered or aligned with a head clamp, exemplarily head clamp 210, via a connection column 302 affixed to the fiducial via a clip 304 and aligned with an opening (not shown) in an arm or strut 306.

Figure 26:
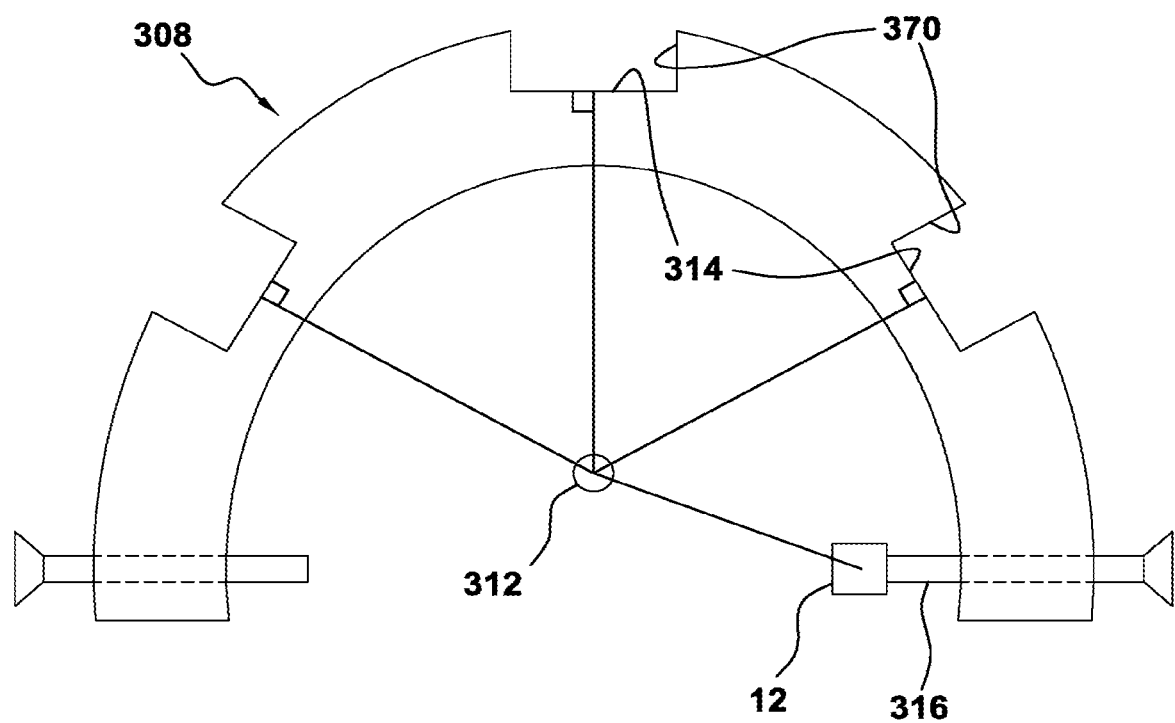
FIG. 26 is a diagrammatic cross-sectional view of a generic head clamp or cranial fixation device, indicating geometric parameters in the design.

FIG. 26 is a two-dimensional representation of an alternative head clamp 308 provided with cavities or recesses 310 rather than apertures as described above with-reference-to FIGS. 17-23. FIG. 26 illustrates how the geometry of the cavities 310 allows for the formation of a focal point 312.

The cavities 310 are designed such that normal vectors 312 extending from the centers of innermost or lower surfaces 314 of the cavities converge to focal point 312, or the relative positions and orientations of the cavity faces are known. The known distances and orientations between the focal point 312 and each of the cavities 310 allows for simplified calculations when constructing an IRA where trackers 18 are seated in cavities 310. The head clamp 308 is fastened to the patient's head using modified pins 316. Secured in a fixed position somewhere on the frame of the head clamp, potentially embedded within a crossbeam 306 spanning the gap between two arms, is a connection column 302 (FIGS. 24 & 25). The connection column 302 locks into both the head clamp and a fiducial 12. Clips 304 found within the body of the connection column 302 lock into the cavities 20 on the interior walls of the fiducial 12. The distance and orientation of the fiducial 12 to the focal point 312 is known due to the fixed construction of the connection column 302 and the head clamp 308. Therefore, the cavities 310 into which the trackers 18 are inserted or seated can be correctly overlaid into a digital image by referencing the fiducial 12.

The head clamp 308 of FIG. 26 enables the use of internal reference array methodology as disclosed hereinabove with reference to the instruments 34.

The invention claimed is:

1. A surgical accessory kit comprising:
   a container;
   a tracking sensor array including a plurality of electronic first active, non-optical tracking devices removably disposed in said container,
   each of said electronic first active, non-optical tracking devices include a casing and a plurality of motion sensors,
   said tracking sensor array further including at least one power source, at least one signal transmitter, and at least one microprocessor all operatively connected to one or more of said electronic first active, non-optical tracking devices; and
   at least one surgical instrument disposed in said container, said at least one surgical instrument being provided with at least one electronic second active, non-optical tracking device fixed to said surgical instrument and including a plurality of motion sensors,
   said at least one surgical instrument being further provided with a power source, a signal transmitter, and a microprocessor all operatively connected to said at least one electronic second active, non-optical tracking device and mounted to said at least one surgical instrument.

2. The surgical accessory kit of claim 1, further comprising at least one fastening component for attaching said tracking sensor array to a patient so that said plurality of electronic first active, non-optical tracking devices are each located at a predetermined position relative to the patient.

3. The surgical accessory kit of claim 2 wherein said at least one fastening component is one of a plurality of fastening components each in the form of a CT or MRI opaque fiducial removably disposed in said container resulting in a plurality of CT or MRI opaque fiducials, each of the CT or MRI opaque fiducials being provided on an underside with an adhesive layer for removably attaching the respective fiducial to the patient, wherein the casings of each of said electronic first active, non-optical tracking devices is attachable to a respective ones of said CT or MRI opaque fiducials resulting in attachable casings.

4. The surgical accessory kit of claim 3 wherein said CT or MRI opaque fiducials are provided on upper sides with respective recesses, said attachable casings of said electronic first active, non-optical tracking devices being seatable in respective ones of said recesses, said CT or MRI opaque fiducials having a coating or layer of CT or MRI opaque material disposed on floors or bottom surfaces of said recesses.

5. The surgical accessory kit of claim 2 wherein said at least one fastening component is a clamp fixable to a patient, said clamp including recesses for seating respective ones of said electronic first active, non-optical tracking devices.

6. The surgical accessory kit of claim 5 wherein said clamp is a head clamp comprising a substantially rigid frame including a plurality of arcuate arms arranged in a predetermined configuration adapted to a neurosurgical approach, said arcuate arms being connected to one another at a hub region, each of said arcuate arms being curved as to fit around a superior half of a patient's head, each of said arcuate arms being provided at a free end with a respective head contact member.

7. The kit of claim 2, wherein the fastening component is a device for fixating a patient's head for a neurosurgical procedure, comprising
   a substantially rigid frame including a plurality of arcuate arms arranged in a predetermined configuration adapted to a neurosurgical approach, said arcuate arms being connected to one another at a hub region, each of said arcuate arms being curved as to fit around a superior half of the patient's head, each of said arcuate arms being provided, at a free end, with a respective head contact member.

8. The kit of claim 7 wherein said head contact member has an arcuate body and a plurality of ends or corners, said head contact member being configured so that said ends or corners are disposable in contact with the patient's head while said body remains spaced from the same.

9. The kit of claim 8 wherein said arcuate body is a plate in the form of a spherical section having at least three ends or corners, said head contact member being configured so that said at least three ends or corners are disposable in contact with the patient's head while a major portion of said plate remains spaced from the same.

10. The kit of claim 7 wherein said arcuate arms include two anterior arcuate arms configured to extend laterally opposite one another anterior to ears of the patient, said arms further including two posterior arcuate arms angled with respect to one another for extending down the back of the patient's head at approximately forty five degrees equidistant from a midsagittal plane of the patient.

11. The kit of claim 7 wherein said arcuate arms include two anterior arcuate arms angled with respect to one another and configured to extend down over the patient's forehead in vertical alignment with respective eyes of the patient, said arcuate arms further including two posterior arcuate arms angled with respect to one another and configured to extend down over the occipital region of the patient's head, said arcuate arms further including an additional arcuate arm configured to extend laterally and anterior to an ear of the patient.

12. The kit of claim 7 wherein said arcuate arms include two anterior arcuate arms each configured to extend laterally and anterior to a respective ear of the patient, said arcuate arms further including an additional anterior arcuate arm configured to extend down over the patient's forehead in vertical alignment with the bridge of the patient's nose, said arcuate arms further including two posterior arcuate arms angled with respect to one another and configured to extend down on one side of the patient's head posterior to one of the patient's ears.

13. The kit of claim 7 wherein said arcuate arms each include a central body portion having longitudinal edges and further include at least two flanges extending from said longitudinal edges perpendicularly to said central body portion.

14. The surgical accessory kit of claim 1 wherein each of said electronic first active, non-optical tracking devices and said at least one electronic second active, non-optical tracking device includes a translation sensor (accelerometer), a (rotation) gyroscopic sensor, and a magnetometer.

15. The surgical accessory kit of claim 14, wherein each of said translation sensor (accelerometer), said (rotation) gyroscopic sensor, and said magnetometer has three degrees of freedom.

16. The surgical accessory kit of claim 15, further comprising a magnetic field calibration sensor disposed in said container.

17. The surgical accessory kit of claim 1, further comprising a calibration sensor disposed in said container.

18. The surgical accessory kit of claim 1, wherein each of said electronic first active, non-optical tracking devices includes a respective power source, a respective signal transmitter, and a respective microprocessor, whereby each of said electronic first active, non-optical tracking devices is autonomous and independent of the others of said electronic first active, non-optical tracking devices.

19. The surgical accessory kit of claim 1, wherein said electronic first active, non-optical tracking devices, at least one fastening component, said at least one surgical instrument, and a magnetic field calibration sensor all occupy respective predetermined positions in said container.

20. The kit of claim 7 wherein said arcuate arms each include a superstructure made of hard and sturdy polymeric material, each of said arms being each coated on an interior or concave side with a layer of resilient material.

21. The kit of claim 1, wherein the plurality of the motion sensors of the electronic first and second active, non-optical tracking devices are inertial measurement units (IMUs) comprising at least one (i) gyroscope, (ii) accelerometer, and/or (iii) magnetometer.

22. The kit of claim 21, wherein the magnetometer is a MEMS (micro-electrical-mechanical system) magnetometer comprising a Hall Effect magnetic sensor.

23. The kit of claim 21, wherein the plurality of motion sensors are three or more sensors that are part of the first and second active, non-optical tracking devices.

24. A surgical apparatus or assembly for use in cooperation with a surgical navigation system, said apparatus or assembly comprising:
at least one surgical instrument having an operative tip or end effector;
a plurality of sensor devices of a non-optical active tracking device each disposed in a predetermined fixed position and predetermined fixed orientation on said at least one surgical instrument, each of the plurality of sensor devices including a plurality of motion sensors;
a microprocessor disposed on or mounted to said at least one surgical instrument and operatively connected to said plurality of sensor devices;
a power source disposed on or mounted to said at least one surgical instrument and operatively connected to said plurality of sensor devices; and
a wireless signal transmitter disposed on or mounted to said at least one surgical instrument and operatively connected to said microprocessor and said power source, wherein each of the said plurality of sensor devices optionally includes a motion sensor that is a gyroscopic element, a motion sensor that is an accelerometer, and a motion sensor that is a Hall Effect magnetic sensor or magnetometer and/or said plurality of sensor devices are optionally fixed to said at least one surgical instrument at predetermined mutually spaced locations thereon.

25. The surgical apparatus or assembly of claim 24 wherein said at least one surgical instrument includes a polymer core and a sturdy external layer on or over said polymer core to provide structural integrity necessary for operative strain, said polymer core having a hollow cavity housing a capsule containing said plurality of sensor devices.

* * * * *